(12) United States Patent
Matsuoka et al.

(10) Patent No.: US 12,016,793 B2
(45) Date of Patent: Jun. 25, 2024

(54) HEATING AND COOLING STIMULATION DEVICE

(71) Applicant: DENSO CORPORATION, Kariya (JP)

(72) Inventors: Takashi Matsuoka, Kariya (JP); Takuya Kataoka, Kariya (JP); Masaru Kakizaki, Kariya (JP); Taiji Kawachi, Kariya (JP); Yuuki Shimizu, Kariya (JP); Hideki Seki, Kariya (JP)

(73) Assignee: DENSO CORPORATION, Kariya (JP)

( * ) Notice: Subject to any disclaimer, the term of this patent is extended or adjusted under 35 U.S.C. 154(b) by 171 days.

(21) Appl. No.: 17/705,769

(22) Filed: Mar. 28, 2022

(65) Prior Publication Data
US 2022/0218516 A1 Jul. 14, 2022

Related U.S. Application Data

(63) Continuation of application No. PCT/JP2020/036351, filed on Sep. 25, 2020.

(30) Foreign Application Priority Data

Oct. 11, 2019 (JP) ................................ 2019-187807

(51) Int. Cl.
*B60N 2/56* (2006.01)
*A61F 7/00* (2006.01)
*B60N 2/00* (2006.01)

(52) U.S. Cl.
CPC ............ *A61F 7/0053* (2013.01); *B60N 2/002* (2013.01); *B60N 2/565* (2013.01); *B60N 2/5657* (2013.01); *A61F 2007/0093* (2013.01)

(58) Field of Classification Search
CPC .......... A61F 7/0053; A61F 2007/0093; B60N 2/002; B60N 2/565; B60N 2/5657
See application file for complete search history.

(56) References Cited

U.S. PATENT DOCUMENTS

| 7,956,758 | B2* | 6/2011 | Hattori | B60N 2/5685 340/576 |
|---|---|---|---|---|
| 9,815,384 | B2* | 11/2017 | Sugiyama | B60K 28/00 |
| 10,112,513 | B2* | 10/2018 | Patrick | B60N 2/5621 |
| 10,173,696 | B2* | 1/2019 | Yamaguchi | A61B 5/18 |

(Continued)

FOREIGN PATENT DOCUMENTS

| JP | 2004284450 A | 10/2004 |
|---|---|---|
| JP | 6094964 B2 | 3/2017 |

(Continued)

*Primary Examiner* — Philip F Gabler
(74) *Attorney, Agent, or Firm* — Harness, Dickey & Pierce, P.L.C.

(57) ABSTRACT

A heating and cooling stimulation device includes a stimulation supply unit configured to supply hot stimulation and cold stimulation to a subject; an estimation unit configured to estimate a fatigue level of the subject; and a control unit configured to control an operation of the stimulation supply unit so as to supply the hot stimulation and the cold stimulation alternately to the subject in accordance with the fatigue level estimated by the estimation unit. The control unit controls the operation of the stimulation supply unit such that an amount of the cold stimulation received by the subject increases as the fatigue level estimated by the estimation unit becomes higher.

14 Claims, 21 Drawing Sheets

(56) References Cited

U.S. PATENT DOCUMENTS

| | | | |
|---|---|---|---|
| 2004/0201481 A1* | 10/2004 | Yoshinori | B60N 2/0244 340/575 |
| 2005/0200166 A1* | 9/2005 | Noh | B60N 2/5657 297/180.14 |
| 2020/0093635 A1 | 3/2020 | Kakizaki et al. | |

FOREIGN PATENT DOCUMENTS

| | | |
|---|---|---|
| JP | 2018193057 A | 12/2018 |
| JP | 2020044156 A | 3/2020 |
| JP | 2021019733 A | 2/2021 |

* cited by examiner

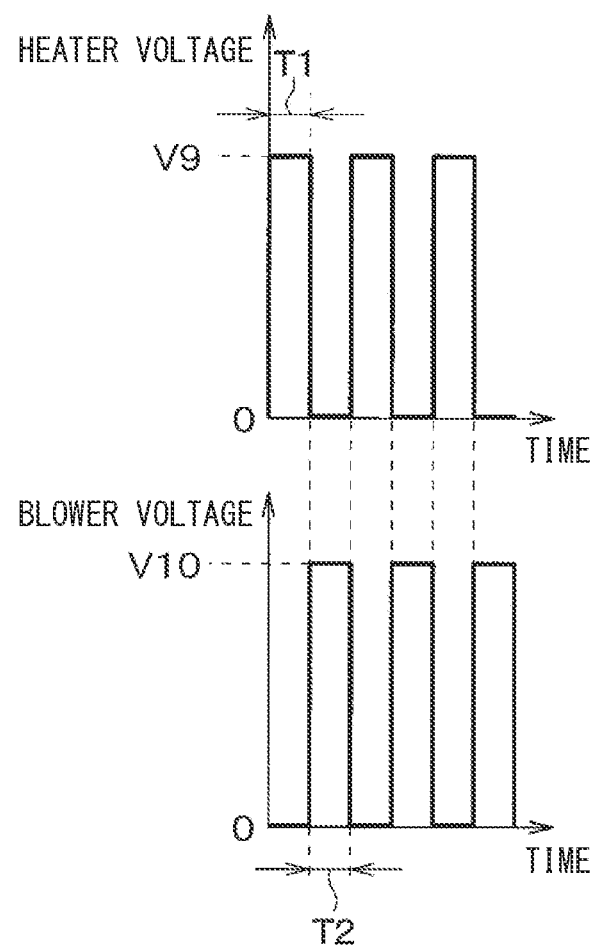

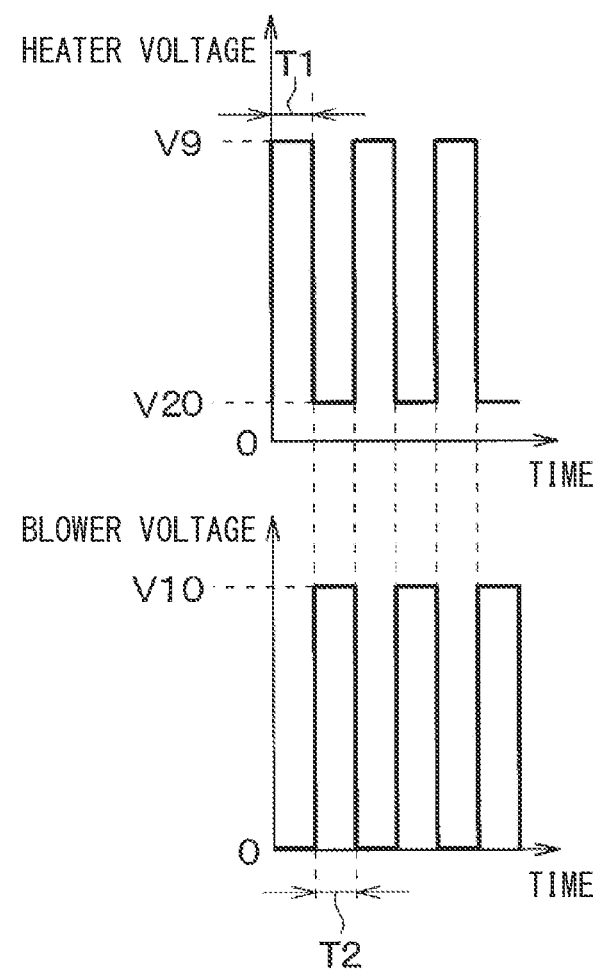

HEATING AND COOLING STIMULATION DEVICE

CROSS REFERENCE TO RELATED APPLICATION

The present application is a continuation application of International Patent Application No. PCT/JP2020/036351 filed on Sep. 25, 2020, which designated the U.S. and claims the benefit of priority from Japanese Patent Application No. 2019-187807 filed on Oct. 11, 2019. The entire disclosures of all of the above applications are incorporated herein by reference.

TECHNICAL FIELD

The present disclosure relates to a heating and cooling stimulation device.

BACKGROUND

A heating and cooling stimulation device can be made to supply hot stimulation and cold stimulation alternately to a subject such as a user.

SUMMARY

According to an exemplar embodiment of the present disclose, a heating and cooling stimulation device includes: a stimulation supply unit configured to supply hot stimulation and cold stimulation to a subject; an estimation unit configured to estimate a fatigue level of the subject; and a control unit configured to control an operation of the stimulation supply unit so as to supply the hot stimulation and the cold stimulation alternately to the subject in accordance with the fatigue level estimated by the estimation unit. In addition, the control unit controls the operation of the stimulation supply unit, to increase an amount of the cold stimulation supplied to the subject, as the fatigue level estimated by the estimation unit becomes higher. Thus, the heating and cooling stimulation device can effectively reduce the fatigue of the subject in accordance with the fatigue level.

BRIEF DESCRIPTION OF THE DRAWINGS

The above and other objects, features and advantages of the present disclosure will become more apparent from the following detailed description made with reference to the accompanying drawings. In the drawings:

FIG. 4E is a time chart illustrating the operation contents of the seat heater and the blower when the fatigue level of the first embodiment is 5;

FIG. 12E is a time chart illustrating the operation contents of the seat heater and the blower when the fatigue level of the fifth embodiment is 5;

DESCRIPTION OF EMBODIMENTS

Figure 1:
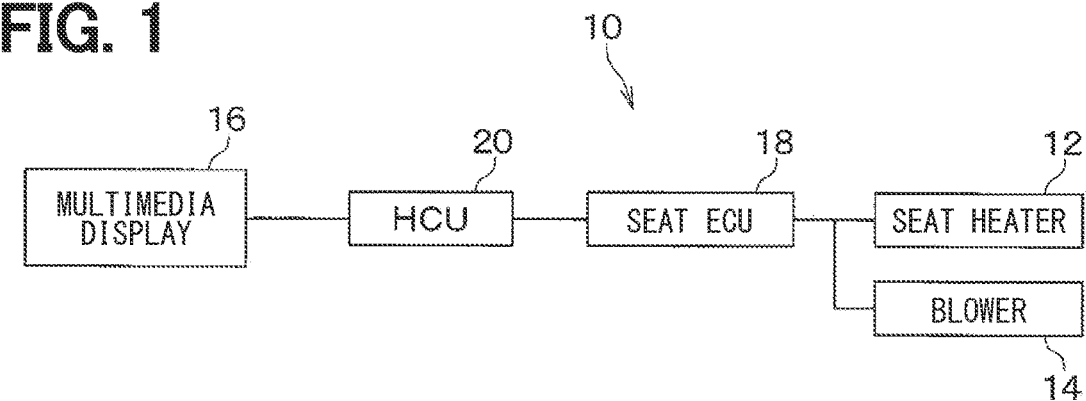
FIG. 1 is a block diagram illustrating an overall configuration of a heating and cooling stimulation device according to a first embodiment.

The inventors of the present application deeply studied an effective reduction in the fatigue of a subject such as a user, in accordance with a fatigue level of the subject.

An object of the present disclosure is to provide a heating and cooling stimulation device that can effectively reduce the fatigue of a subject in accordance with the fatigue level of the subject.

To achieve the above object, according to an exemplar embodiment of the present disclose, a heating and cooling stimulation device is provided with a controller configured to estimate a fatigue level of the subject, and configured to control an operation of a stimulation supply unit so as to supply a hot stimulation and a cold stimulation alternately to the subject in accordance with the estimated fatigue level. In addition, the controller controls the operation of the stimulation supply unit, to increase an amount of the cold stimulation supplied to the subject, as the estimated fatigue level becomes higher.

The heating and cooling stimulation device supplies hot stimulation and cold stimulation alternately to the subject. Thus, the effect of improving a blood flow is obtained by a pumping action exerted by widening and narrowing blood vessels. Furthermore, the heating and cooling stimulation device increases the amount of cold stimulation supplied to the subject as the fatigue level becomes higher. Thus, a difference between the amount of hot stimulation and the amount of cold stimulation increases as the fatigue level of the subject becomes higher, thereby accelerating the pumping action exerted by widening and narrowing blood vessels. Hence, the effect of improving the blood flow can be enhanced.

For this reason, the heating and cooling stimulation device can effectively reduce the fatigue of the subject in accordance with the fatigue level.

Next, embodiments of the present disclosure will be described below in accordance with the accompanying drawings. In the following embodiments, identical or equivalent parts are described with the same reference numerals.

First Embodiment

A heating and cooling stimulation device 10 according to the present embodiment illustrated in FIG. 1 is installed in a vehicle. The heating and cooling stimulation device 10 includes a seat heater 12, a blower 14, a multimedia display 16, a seat ECU 18, and an HCU 20.

The seat heater 12 and the blower 14 are stimulation supply units that supply hot stimulation and cold stimulation to a passenger serving as a subject. Hot stimulation is thermal stimulation at a higher temperature than the body temperature of the subject. The cold stimulation is thermal stimulation at a lower temperature than the body temperature of the subject.

Figure 2:
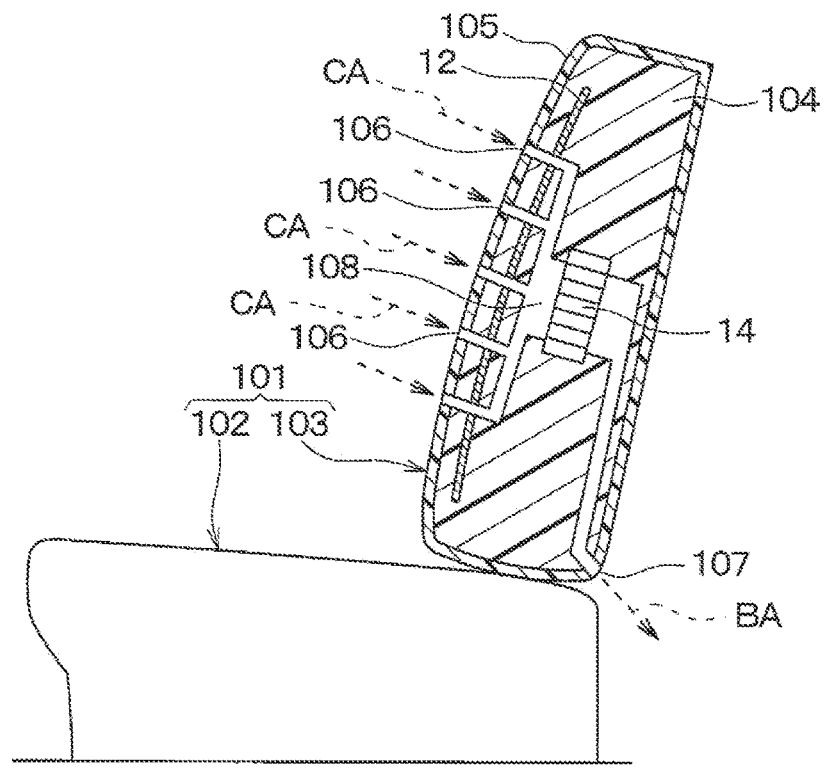
FIG. 2 is a cross-sectional view of a seat provided with a seat heater and a blower for the heating and cooling stimulation device according to the first embodiment.

As illustrated in FIG. 2, the seat heater 12 and the blower 14 are installed in a driver's seat 101 provided for a vehicle. The seat 101 has a seating portion 102 that supports the hip and thighs of a passenger seated on the seat 101 (that is, a seated person) and a backrest portion 103 that supports the back of the passenger. The front side of the backrest portion 103 is in contact with the passenger. The back side of the backrest portion is opposed to the front side in contact with the passenger. The backrest portion 103 includes a seat pad 104 composed of an elastic material and a skin material 105 covering the seat pad 104.

The seat heater 12 is provided in the backrest portion 103 so as to extend over the front side of the backrest portion 103. The seat heater 12 generates heat by energization. Heat from the seat heater 12 is supplied to a passenger by radiation or heat conduction. Thus, hot stimulation is supplied to the passenger.

The blower 14 is provided in the backrest portion 103. Specifically, the skin material 105 has a plurality of air inlets 106 on the front side of the backrest portion 103. The skin material 105 has at least one air outlet 107 on the back side of the backrest portion 103. The seat pad 104 has an air passage 108 from the air inlets 106 to the at least one air outlet 107. The blower 14 is disposed at the midpoint of the air passage 108.

By operating the blower 14, air in the vehicle is drawn from the air inlets 106 into the air passage 108 as illustrated by dashed arrows CA in FIG. 2. The drawn air passes through the air passage 108 and is then blown out of at least the air outlet 107 as illustrated by a dashed arrow BA in FIG. 2. In this way, by operating the blower 14, air in the vehicle is drawn into the backrest portion 103.

During the driving of the vehicle, the back of a passenger seated on the driver's seat is separated from the backrest portion 103. Generally, in a vehicle provided with an air conditioner, the air temperature in the vehicle is kept lower than the body temperature of the passenger by an operation of the air conditioner. Hence, by operating the blower 14, air in the vehicle is drawn into the backrest portion 103, so that air having a lower temperature than the body temperature of the passenger passes near the back of the passenger. The air cools the shoulders, back, and hips of the passenger. In other words, the cold stimulation is supplied to the back of the passenger to reach the shoulders, back, and hips of the passenger. Even when the back of the passenger is in contact with the backrest portion 103, air in the vehicle is drawn into the backrest portion 103 through a gap between the back of the passenger and the backrest portion 103. The air cools the shoulders, back, and hips of the passenger.

The multimedia display 16 is installed on an instrument panel disposed in front of a front seat in the vehicle. The multimedia display 16 is a display/input unit for inputting information by an operation of the passenger while displaying a screen. Specifically, the multimedia display 16 includes a display main unit for displaying the screen and a touch panel provided on the surface of the display main unit. The touch panel outputs a signal corresponding to the position of an operating body, for example, a finger placed on the surface of the touch panel.

Figure 3:
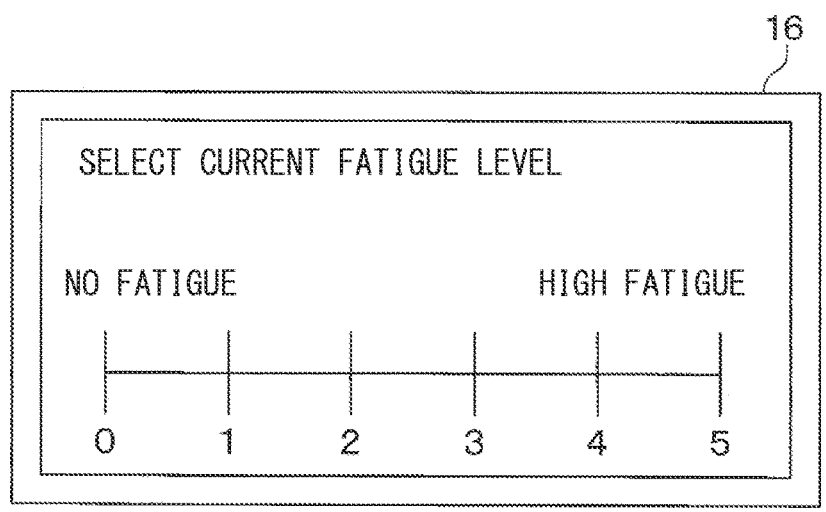
FIG. 3 is a diagram illustrating a display screen of a multimedia display provided for the heating and cooling stimulation device according to the first embodiment.

In the present embodiment, in response to an operation of the touch panel by a passenger, information about the fatigue level of the passenger is inputted from the multimedia display 16. Specifically, the multimedia display 16 displays the tool button of a fatigue reduction mode. When the tool button is selected by the passenger, the multimedia display 16 displays a fatigue-level selection screen as illustrated in FIG. 3. The selection screen displays an axis of fatigue at six levels from "no fatigue" to "extreme fatigue" sequentially from the left. The axis indicates fatigue levels of 0, 1, 2, 3, 4, and 5 sequentially from the left. The fatigue level becomes higher as the numeric value increases. The passenger operates the touch panel to select a fatigue level closest to the current state of the passenger. Thus, operation information on the touch panel is transmitted to the HCU 20.

The seat ECU 18 is one of the electronic control units installed in the vehicle. The ECU 18 is an abbreviation for Electronic Control Unit. The seat ECU 18 is composed of a processor, a microcomputer including memory, and a peripheral circuit thereof. The memory includes a non-transitory tangible storage medium. The seat ECU 18 performs various operations and processing according to programs stored in the memory. Thus, the seat ECU 18 operates the seat heater 12 and the blower 14 so as to supply the hot stimulation and the cold stimulation alternately to the passenger. Hereinafter, the supply of the hot stimulation and the cold stimulation alternately to the passenger may be simply referred to as heating and cooling stimulation.

Figure 4A:
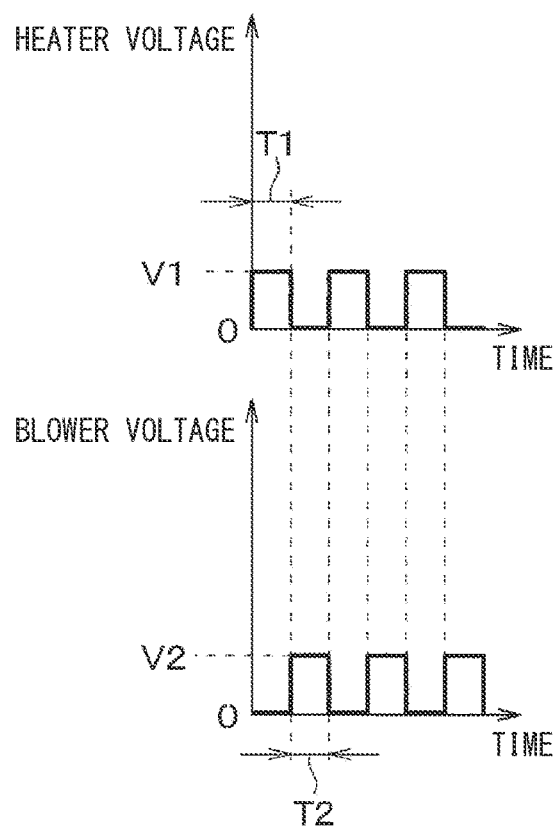
FIG. 4A is a time chart illustrating the operation contents of the seat heater and the blower when the fatigue level of the first embodiment is 1.

Specifically, as illustrated in FIG. 4A, the seat ECU 18 controls voltages to the seat heater and the blower so as to alternately repeat a hot-stimulation supply state in which a heater voltage is "large" and a blower voltage is "small" and a cold-stimulation supply state in which a heater voltage is "small" and a blower voltage is "large." The heater voltage is a voltage to be supplied to the heater. The blower voltage is a voltage to be supplied to the blower. The hot-stimulation supply state is a state in which the seat heater 12 is operated to supply the hot stimulation to the passenger. The cold-stimulation supply state is a state in which the blower 14 is operated to supply the cold stimulation to the passenger. In FIG. 4A, the hot-stimulation supply state is obtained at a heater voltage of V1 and a blower voltage of 0. The cold-stimulation supply state is obtained at a heater voltage of 0 and a blower voltage of V2. In FIG. 4A, when a fan voltage is "small," the voltage is "0", and when a heater voltage is "small," the voltage is "0."

Specifically, in the present embodiment, the seat ECU 18 controls the on and off of the seat heater 12 and the blower 14 so as to alternately repeat a hot-stimulation supply state in which the seat heater 12 is turned on while the blower 14 is turned off and a cold-stimulation supply state in which the seat heater 12 is turned off while the blower 14 is turned on.

The HCU 20 is one of electronic control units installed in the vehicle. The HCU 20 is an abbreviation for HMI Control Unit. The HMI is an abbreviation for Human Machine Interface. The HCU 20 is electrically connected to the seat ECU 18. Moreover, the HCU 20 is electrically connected to the multimedia display 16.

The HCU 20 estimates the fatigue level of a passenger based on information inputted from the multimedia display 16. The HCU 20 transmits the operation contents of the seat heater 12 and the blower 14 to the seat ECU 18 in accordance with the estimated fatigue level.

Figure 5:
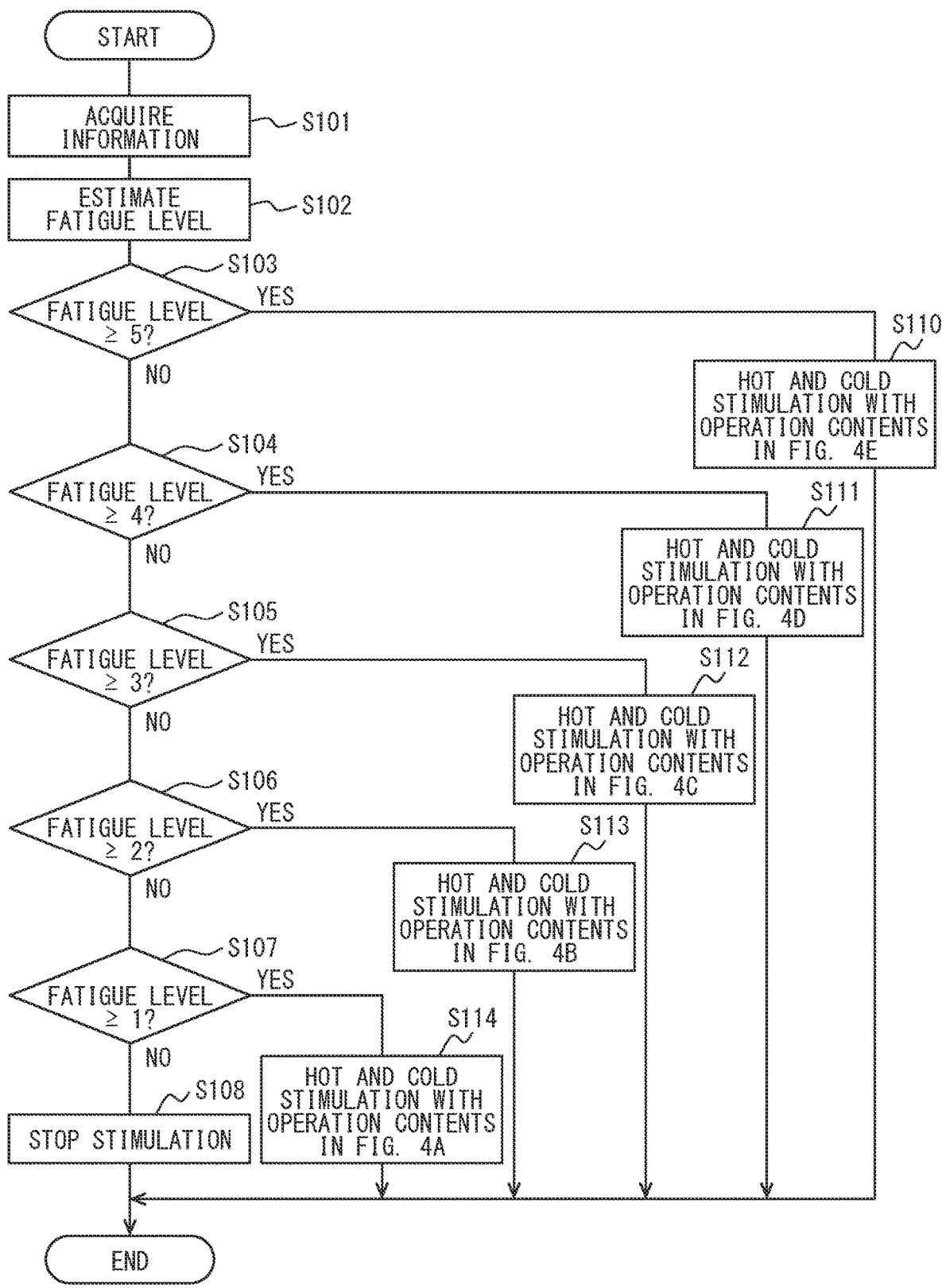
FIG. 5 is a flowchart illustrating the control processing of an HCU provided for the heating and cooling stimulation device according to the first embodiment.

The HCU 20 is composed of a processor, a microcomputer including memory, and a peripheral circuit thereof. The memory includes a non-transitory tangible storage medium. The HCU 20 performs various operations and processing according to programs stored in the memory. With this configuration, control processing illustrated in FIG. 5 is performed. The control processing will be described later.

Figure 4B:
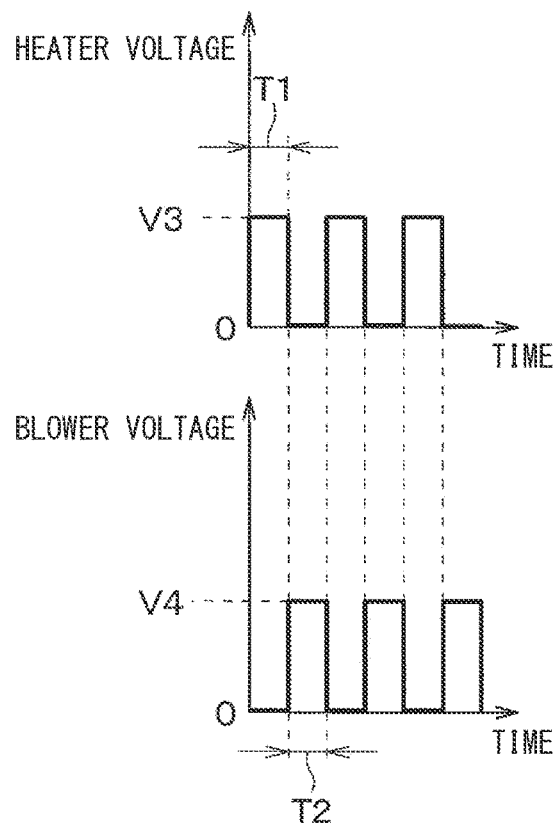
FIG. 4B is a time chart illustrating the operation contents of the seat heater and the blower when the fatigue level of the first embodiment is 2.
Figure 4C:
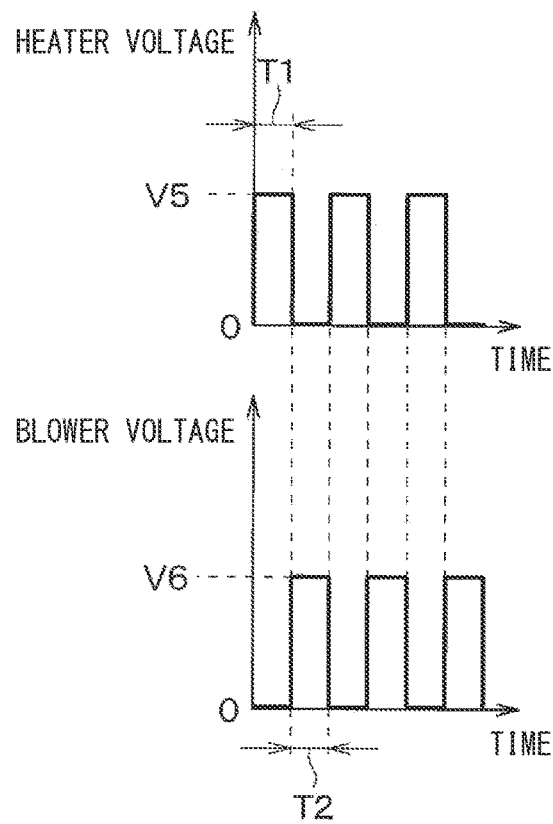
FIG. 4C is a time chart illustrating the operation contents of the seat heater and the blower when the fatigue level of the first embodiment is 3.
Figure 4D:
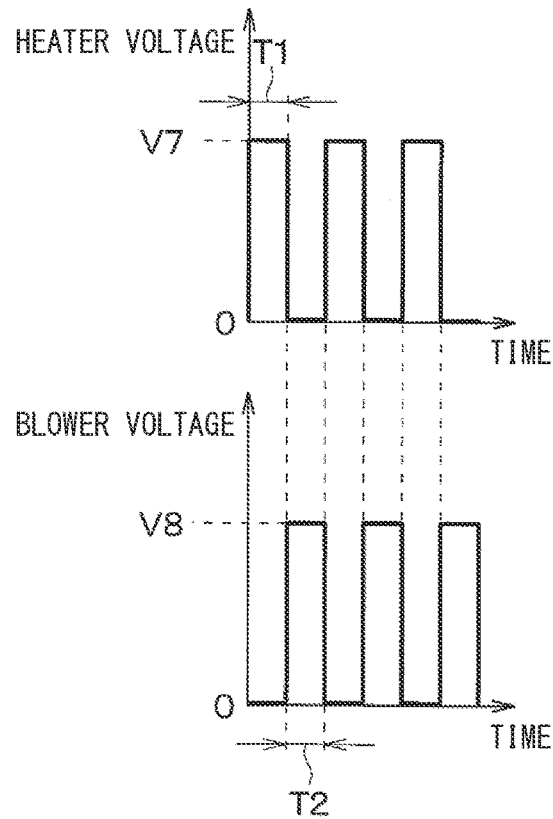
FIG. 4D is a time chart illustrating the operation contents of the seat heater and the blower when the fatigue level of the first embodiment is 4.

In the memory of the HCU 20, respective operation contents illustrated in FIGS. 4A, 4B, 4C, 4D, and 4E are stored in advance as the operation contents of the seat heater 12 and the blower 14 in accordance with the estimated fatigue level. FIG. 4A indicates the operation contents when the fatigue level is 1. FIG. 4B indicates the operation contents when the fatigue level is 2. FIG. 4C indicates the operation contents when the fatigue level is 3. FIG. 4D indicates the operation contents when the fatigue level is 4. FIG. 4E indicates the operation contents when the fatigue level is 5.

In FIGS. 4A to 4E, the hot-stimulation supply state and the cold-stimulation supply state are alternately performed. At this point, the heater voltage of the hot-stimulation supply state and the operating time of the seat heater 12 are kept constant. At this point, the blower voltage of the cold-stimulation supply state and the operating time of the blower 14 are kept constant. In this way, the hot stimulation and the cold stimulation are alternately supplied with constant stimulation intensity.

In FIGS. 4A to 4E, V1, V3, V5, V7, and V9 denote heater voltages in the hot-stimulation supply state. The relationship among the heater voltages is established as follows:

$$V1 < V3 < V5 < V7 < V9$$

In FIGS. 4A to 4E, V2, V4, V6, V8, and V10 denote blower voltages in the cold-stimulation supply state. The relationship among the blower voltages is established as follows:

$$V2 < V4 < V6 < V8 < V10$$

In FIGS. 4A to 4E, the operating time of the seat heater 12 is kept at T1 in the hot-stimulation supply state. The operating time of the blower 14 is kept at T2 in the cold-stimulation supply state.

In the operation contents illustrated in FIGS. 4A to 4E, the heater voltage and the blower voltage increase as the estimated fatigue level becomes higher. In other words, the intensity of the hot stimulation supplied by the seat heater 12 and the intensity of the cold stimulation supplied by the blower 14 increase as the estimated fatigue level becomes higher. Thus, the stimulation amounts of the hot stimulation and the cold stimulation received by a passenger increase as the fatigue level becomes higher.

In this case, the stimulation amounts of the hot stimulation and the cold stimulation indicate the amounts of thermal energy supplied to a subject. The amounts of the hot stimulation can be compared with each other by using at least one of a heater voltage per unit time in the hot-stimulation supply state and the operating time of the seat heater 12 in the hot-stimulation supply state. The amounts of the hot stimulation are compared with each other while keeping the operating time of the seat heater 12 constant in the hot-stimulation supply state. In this case, as the heater voltage per unit time increases in the hot-stimulation supply state, the amount of heat generated by the seat heater 12 increases, thereby supplying a larger amount of thermal energy to the subject. Hence, in the present embodiment, the amount of the hot stimulation received by the passenger increases as the fatigue level becomes higher.

Likewise, the amounts of the cold stimulation can be compared with each other by using at least one of a blower voltage per unit time in the cold-stimulation supply state and the operating time of the blower 14 in the cold-stimulation supply state. The amounts of the cold stimulation are compared with each other while keeping the operating time of the blower 14 constant in the cold-stimulation supply state.

In this case, as the blower voltage per unit time increases in the cold-stimulation supply state, the volume of air from the blower 14 increases, thereby passing a larger volume of air near the back of the passenger. Thus, a larger amount of thermal energy is drawn from the subject. In other words, a larger amount of cold energy is supplied to the subject. Hence, in the present embodiment, the amount of the cold stimulation received by the passenger increases as the fatigue level becomes higher.

The control processing performed by the HCU 20 as illustrated in FIG. 5 will be described below. The respective steps illustrated in FIG. 5 correspond to functional parts for implementing various functions. The control processing is performed when the passenger selects the display of the fatigue reduction mode illustrated on the multimedia display 16. When the display is not selected by the passenger, the control processing is not performed.

In S101, the HCU 20 acquires information on the fatigue level. As the information on the fatigue level, information inputted by a touch panel operation by the passenger is acquired. The information inputted by the passenger is operation information on the touch panel, the information illustrating the position of a touch or approach of the passenger to the screen.

In step S102, the HCU 20 estimates the fatigue level of the passenger based on the information acquired in step S101. In the present embodiment, the HCU 20 specifies one of 0 to 5 as the fatigue level selected by the passenger, from the operation information on the touch panel.

Subsequently, in step S103, the HCU 20 determines whether the fatigue level estimated in step S102 is at least 5. When the fatigue level is 5, the HCU 20 determines YES and proceeds to step S110. In step S110, the HCU 20 transmits, to the seat ECU 18, an operation instruction to perform hot and cold stimulation according to the operation contents in FIG. 4E that correspond to the fatigue level of 5. The seat ECU 18 operates the seat heater 12 and the blower 14 according to stimulation intensity illustrated in FIG. 4E. Thus, hot stimulation and cold stimulation are alternately supplied to the passenger. At this point, the passenger receives the largest stimulation amounts of hot stimulation and cold stimulation.

In step S103, when the fatigue level is lower than 5, the HCU 20 determines NO and proceeds to step S104. In step S104, the HCU 20 determines whether the fatigue level estimated in step S102 is at least 4. When the fatigue level is 4, the HCU 20 determines YES and proceeds to step S111. In step S111, the HCU 20 transmits, to the seat ECU 18, an operation instruction to perform hot and cold stimulation according to the operation contents in FIG. 4D that correspond to the fatigue level of 4. The seat ECU 18 operates the seat heater 12 and the blower 14 according to stimulation intensity illustrated in FIG. 4D. Thus, the hot stimulation and the cold stimulation are alternately supplied to the passenger. At this point, the passenger receives the second largest stimulation amounts of the hot stimulation and the cold stimulation.

In step S104, when the fatigue level is lower than 4, the HCU 20 determines NO and proceeds to step S105. In step S105, the HCU 20 determines whether the fatigue level estimated in step S102 is at least 3. When the fatigue level is 3, the HCU 20 determines YES and proceeds to step S112. In step S112, the HCU 20 transmits, to the seat ECU 18, an operation instruction to perform hot and cold stimulation according to the operation contents in FIG. 4C that correspond to the fatigue level of 3. The seat ECU 18 operates the seat heater 12 and the blower 14 according to stimulation intensity illustrated in FIG. 4C. Thus, the hot stimulation and the cold stimulation are alternately supplied to the passenger. At this point, the passenger receives the third largest stimulation amounts of the hot stimulation and the cold stimulation.

In step S105, when the fatigue level is lower than 3, the HCU 20 determines NO and proceeds to step S106. In step S106, the HCU 20 determines whether the fatigue level estimated in step S102 is at least 2. When the fatigue level is 2, the HCU 20 determines YES and proceeds to step S113. In step S113, the HCU 20 transmits, to the seat ECU 18, an operation instruction to perform hot and cold stimulation according to the operation contents in FIG. 4B that correspond to the fatigue level of 2. The seat ECU 18 operates the seat heater 12 and the blower 14 according to stimulation intensity illustrated in FIG. 4B. Thus, the hot stimulation and the cold stimulation are alternately supplied to the passenger. At this point, the passenger receives the fourth largest stimulation amounts of the hot stimulation and the cold stimulation.

In step S106, when the fatigue level is lower than 2, the HCU 20 determines NO and proceeds to step S107. In step S107, the HCU 20 determines whether the fatigue level estimated in step S102 is at least 1. When the fatigue level is 1, the HCU 20 determines YES and proceeds to step S114. In step S114, the HCU 20 transmits, to the seat ECU 18, an operation instruction to perform hot and cold stimulation according to the operation contents in FIG. 4A that correspond to the fatigue level of 1. The seat ECU 18 operates the seat heater 12 and the blower 14 according to stimulation intensity illustrated in FIG. 4A. Thus, the hot stimulation and the cold stimulation are alternately supplied to the passenger. At this point, the passenger receives the fifth largest stimulation amounts of the hot stimulation and the cold stimulation.

In step S107, when the fatigue level is 0, the HCU 20 determines NO and proceeds to step S108. In step S108, the HCU 20 transmits, to the seat ECU 18, an instruction to stop the hot and cold stimulation. The seat ECU 18 stops the seat heater 12 and the blower 14. Thus, the hot and cold stimulation is not supplied to the passenger.

After steps S110, S111, S112, S113, and S114 are performed, the screen of FIG. 3 is displayed again, and control processing illustrated in FIG. 5 is performed. The control processing illustrated in FIG. 5 is not repeated when step S108 is performed and when the passenger selects the termination of the fatigue reduction mode.

As described above, according to the heating and cooling stimulation device 10 of the present embodiment, the HCU 20 estimates the fatigue level of the passenger in step S102. In steps S110, S111, S112, S113, and S114, the HCU 20 indirectly controls the operations of the seat heater 12 and the blower 14 so as to supply the hot stimulation and the cold stimulation alternately to the passenger in accordance with the estimated fatigue level.

Thus, the hot stimulation and the cold stimulation are alternately supplied to the passenger when the passenger becomes fatigued. The supply of the cold stimulation cools a human body so as to narrow blood vessels. The supply of the hot stimulation warms a human body so as to widen blood vessels. Thus, the alternate hot stimulation and cold stimulation causes a pumping action exerted by widening and narrowing of blood vessels, thereby obtaining the effect of improving a blood flow.

Furthermore, in steps S110 to S114, the HCU 20 controls the operation of the seat heater 12 such that the intensity of the hot stimulation supplied by the seat heater 12 increases as the estimated fatigue level becomes higher. The HCU 20 controls the operation of the blower 14 such that the intensity of the cold stimulation supplied by the blower 14 increases as the estimated fatigue level becomes higher. In this way, the HCU 20 controls the operations of the seat heater 12 and the blower 14 such that the amount of the hot stimulation received by the passenger and the amount of the cold stimulation received by the passenger increase as the estimated fatigue level becomes higher.

With this configuration, a difference between the amount of the hot stimulation and the amount of the cold stimulation increases as the fatigue level of the subject becomes higher, thereby accelerating the pumping action exerted by widening and narrowing of blood vessels. Hence, the effect of improving the blood flow can be enhanced as the fatigue level of the passenger becomes higher. For this reason, the heating and cooling stimulation device 10 can effectively reduce the fatigue of the passenger in accordance with the fatigue level of the subject.

In the present embodiment, step S102 corresponds to the estimation unit that estimates the fatigue level of the subject. Steps S110, S111, S112, S113, and S114 correspond to the control unit that controls the operation of the stimulation supply unit so as to supply the hot stimulation and the cold stimulation alternately to the subject in accordance with the fatigue level estimated by the estimation unit.

Second Embodiment

In the present embodiment, control processing performed by an HCU 20 is partially changed from that of the first embodiment. Other configurations of a heating and cooling stimulation device 10 are identical to those of the first embodiment. Different points from the first embodiment will be described below.

Figure 6A:
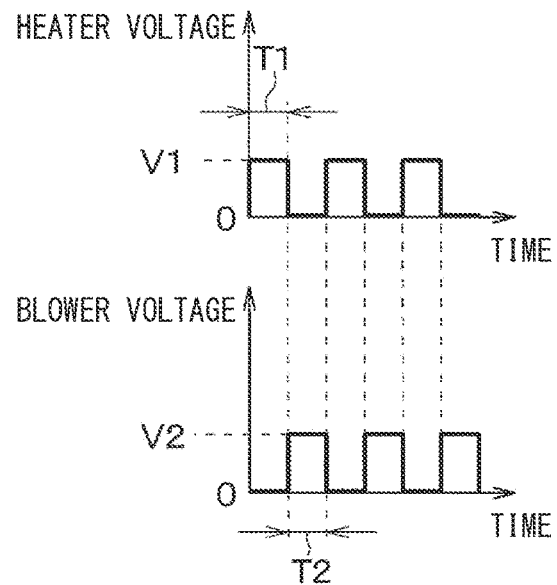
FIG. 6A is a time chart illustrating the operation contents of a seat heater and a blower when the fatigue level of a second embodiment is 1.
Figure 6B:
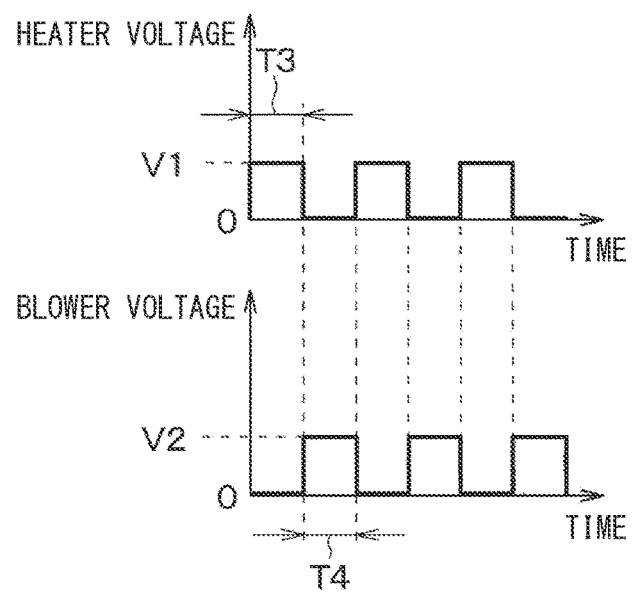
FIG. 6B is a time chart illustrating the operation contents of the seat heater and the blower when the fatigue level of the second embodiment is 2.
Figure 6C:
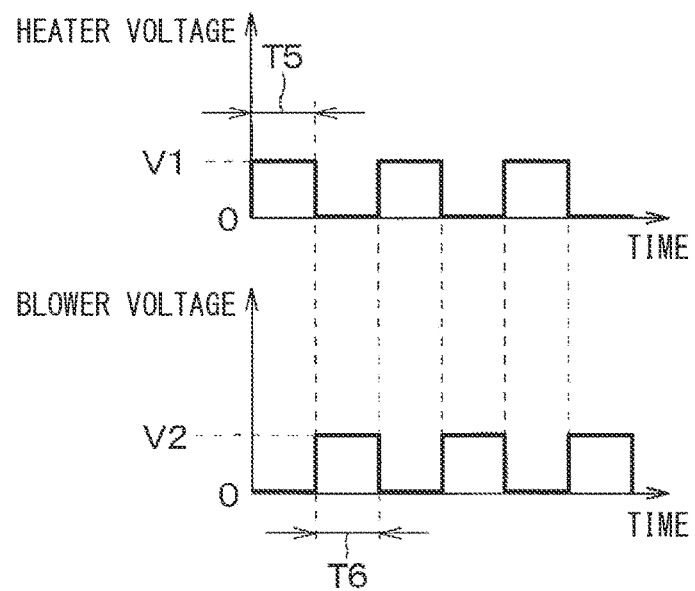
FIG. 6C is a time chart illustrating the operation contents of the seat heater and the blower when the fatigue level of the second embodiment is 3.
Figure 6D:
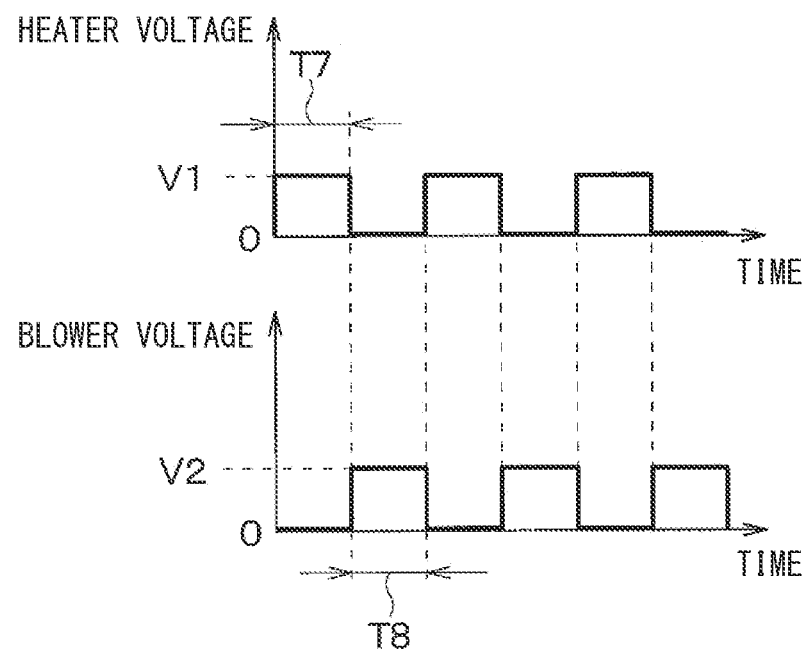
FIG. 6D is a time chart illustrating the operation contents of the seat heater and the blower when the fatigue level of the second embodiment is 4.
Figure 6E:
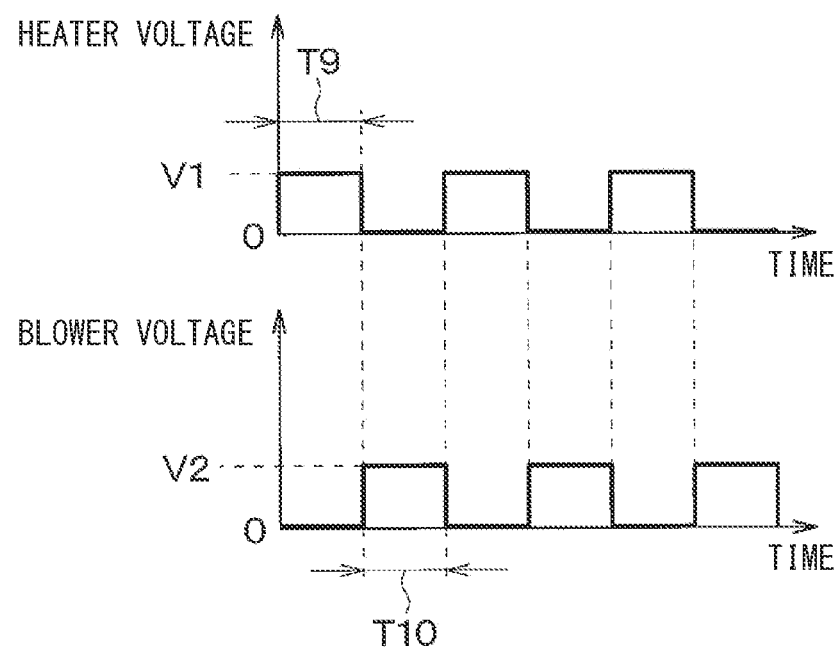
FIG. 6E is a time chart illustrating the operation contents of the seat heater and the blower when the fatigue level of the second embodiment is 5.

In the present embodiment, in the memory of the HCU 20, respective operation contents illustrated in FIGS. 6A, 6B, 6C, 6D, and 6E are stored in advance as the operation contents of a seat heater 12 and a blower 14 in accordance with an estimated fatigue level. FIG. 6A indicates the operation contents when the fatigue level is 1. FIG. 6B indicates the operation contents when the fatigue level is 2. FIG. 6C indicates the operation contents when the fatigue level is 3. FIG. 6D indicates the operation contents when the fatigue level is 4. FIG. 6E indicates the operation contents when the fatigue level is 5.

In FIGS. 6A to 6E, T1, T3, T5, T7, and T9 indicate the operating times of the seat heater 12 in a hot-stimulation supply state. The relationship among the operating times is established as follows:

T1<T3<T5<T7<T9

In FIGS. 6A to 6E, T2, T4, T6, T8, and T10 denote the operating times of the blower 14 in a cold-stimulation supply state. The relationship among the operating times is established as follows:

T2<T4<T6<T8<T10

In FIGS. 6A to 6E, a heater voltage is kept at V1 in the hot-stimulation supply state. A blower voltage is kept at V2 in the cold-stimulation supply state.

In the operation contents illustrated in FIGS. 6A to 6E, as the estimated fatigue level becomes higher, the operating time of the seat heater 12 in the hot-stimulation supply state increases, and the operating time of the blower 14 in the cold-stimulation supply state increases. The operating times are compared with each other while keeping a heater voltage in the hot-stimulation supply state. In this case, as the operating time of the seat heater 12 increases in the hot-stimulation supply state, the amount of thermal energy supplied to a subject increases. Similar to the hot-stimulation supply state, the operating times are compared with each other while keeping a blower voltage in the cold-stimulation supply state. In this case, as the operating time of the blower 14 increases in the cold-stimulation supply state, the amount of thermal energy drawn from the subject increases. In other words, a larger amount of cold energy is supplied to the subject. Thus, also in the present embodiment, the stimulation amounts of hot stimulation and cold stimulation received by a passenger increase as the fatigue level becomes higher.

Figure 7:
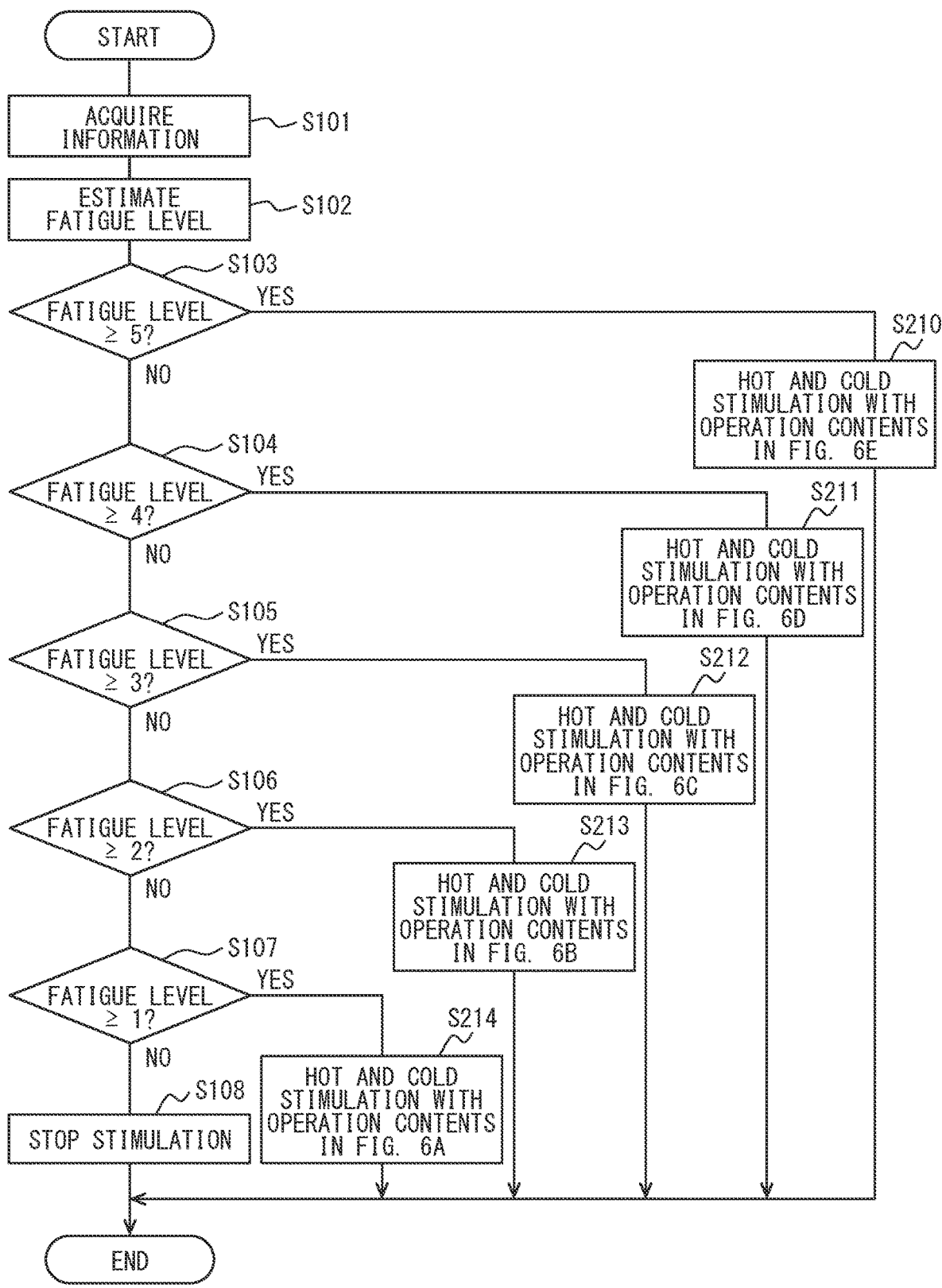
FIG. 7 is a flowchart illustrating the control processing of an HCU according to the second embodiment.

The HCU 20 performs control processing illustrated in FIG. 7. The control processing illustrated in FIG. 7 is different from the control processing illustrated in FIG. 5 in that steps S110, S111, S112, S113, and S114 are replaced with steps S210, S211, S212, S213, and S214. Steps S210, S211, S212, S213, and S214 correspond to a control unit that controls the operation of a stimulation supply unit so as to supply the hot stimulation and the cold stimulation alternately to the subject in accordance with the fatigue level estimated by an estimation unit.

When the fatigue level estimated in step S102 is 5, the HCU 20 in step S210 transmits, to a seat ECU 18, an operation instruction to perform the hot and cold stimulation according to the operation contents in FIG. 6E that correspond to the fatigue level of 5. The seat ECU 18 operates the seat heater 12 and the blower 14 according to the operation contents illustrated in FIG. 6E.

When the fatigue level estimated in step S102 is 4, the HCU 20 in step S211 transmits, to the seat ECU 18, an operation instruction to perform the hot and cold stimulation according to the operation contents in FIG. 6D that correspond to the fatigue level of 4. The seat ECU 18 operates the seat heater 12 and the blower 14 according to the operation contents illustrated in FIG. 6D.

When the fatigue level estimated in step S102 is 3, the HCU 20 in step S212 transmits, to the seat ECU 18, an operation instruction to perform the hot and cold stimulation according to the operation contents in FIG. 6C that correspond to the fatigue level of 5. The seat ECU 18 operates the seat heater 12 and the blower 14 according to the operation contents illustrated in FIG. 6C.

When the fatigue level estimated in step S102 is 2, the HCU 20 in step S213 transmits, to the seat ECU 18, an operation instruction to perform the hot and cold stimulation according to the operation contents in FIG. 6B that correspond to the fatigue level of 5. The seat ECU 18 operates the seat heater 12 and the blower 14 according to the operation contents illustrated in FIG. 6B.

When the fatigue level estimated in step S102 is 1, the HCU 20 in step S214 transmits, to the seat ECU 18, an operation instruction to perform the hot and cold stimulation according to the operation contents in FIG. 6A that correspond to the fatigue level of 5. The seat ECU 18 operates the seat heater 12 and the blower 14 according to the operation contents illustrated in FIG. 6A.

As described above, according to the heating and cooling stimulation device 10 of the present embodiment, the HCU 20 in steps S210 to S214 controls the operation of the seat heater 12 such that the operating time of the seat heater 12 during which the seat heater 12 supplies the hot stimulation is elongated as the estimated fatigue level becomes higher. The HCU 20 controls the operation of the blower 14 such that the operating time of the blower 14 is elongated during which the blower 14 supplies the cold stimulation as the estimated fatigue level becomes higher. In this way, the HCU 20 controls the operations of the seat heater 12 and the blower 14 such that the amount of the hot stimulation received by the passenger and the amount of the cold stimulation received by the passenger increase as the estimated fatigue level becomes higher. Thus, also in the present embodiment, the same effect as the first embodiment is obtained.

Third Embodiment

In the present embodiment, control processing performed by an HCU 20 is partially changed from that of the first embodiment. Other configurations of a heating and cooling stimulation device 10 are identical to those of the first embodiment. Different points from the first embodiment will be described below. The present embodiment corresponds to a combination of the first embodiment and the second embodiment.

Figure 8A:
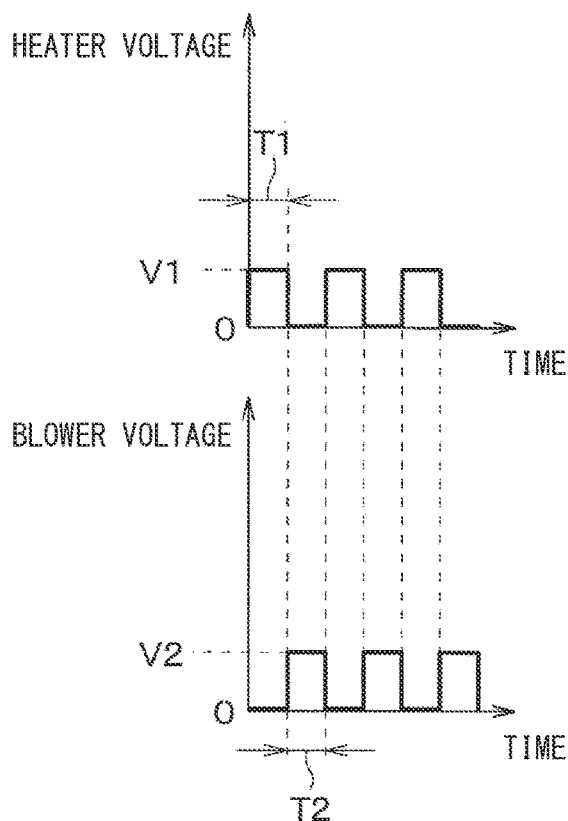
FIG. 8A is a time chart illustrating the operation contents of a seat heater and a blower when the fatigue level of a third embodiment is 1.
Figure 8B:
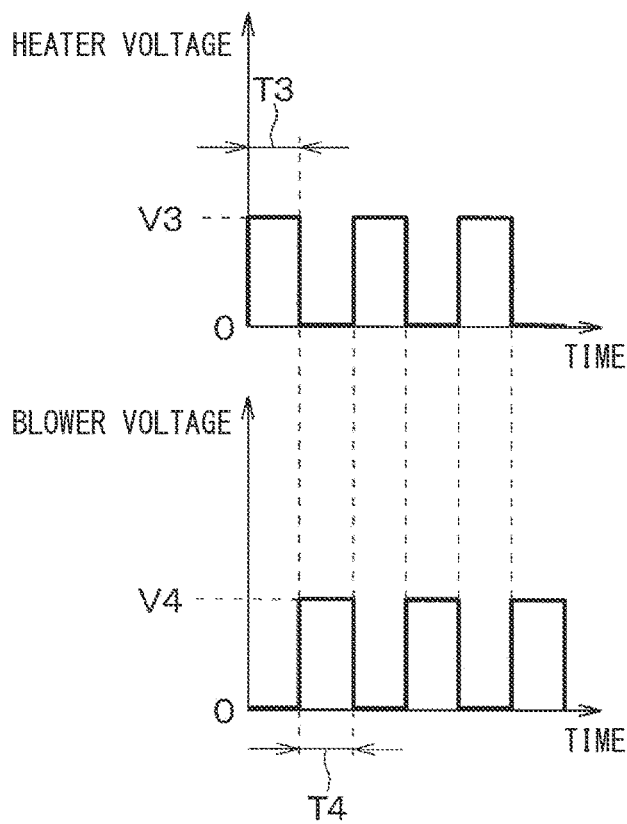
FIG. 8B is a time chart illustrating the operation contents of the seat heater and the blower when the fatigue level of the third embodiment is 2.
Figure 8C:
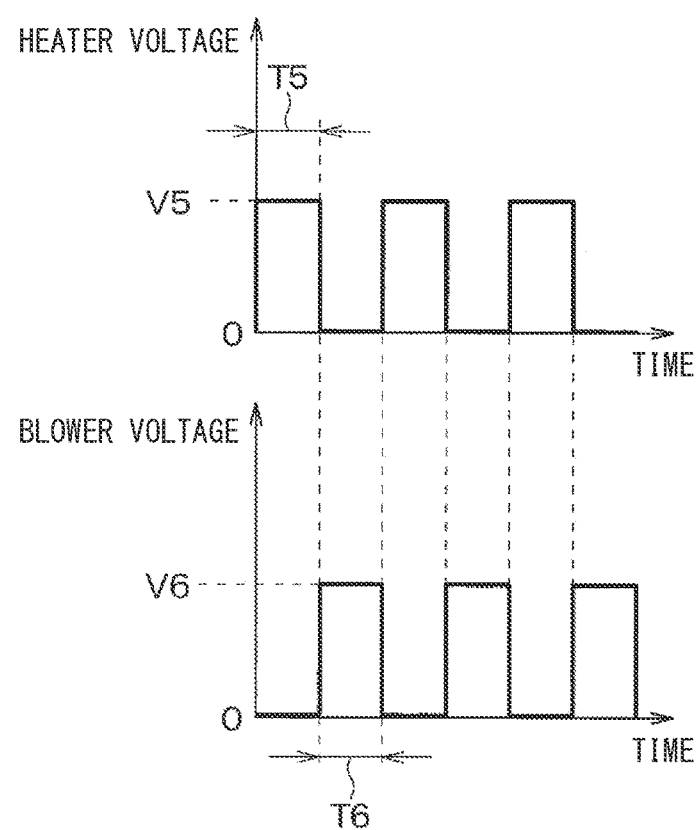
FIG. 8C is a time chart illustrating the operation contents of the seat heater and the blower when the fatigue level of the third embodiment is 3.
Figure 8D:
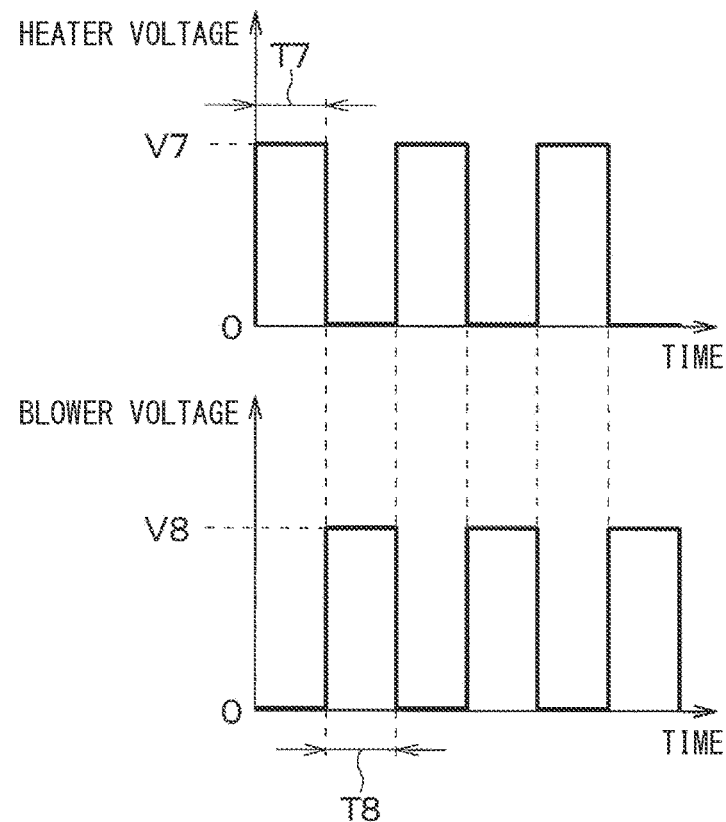
FIG. 8D is a time chart illustrating the operation contents of the seat heater and the blower when the fatigue level of the third embodiment is 4.
Figure 8E:
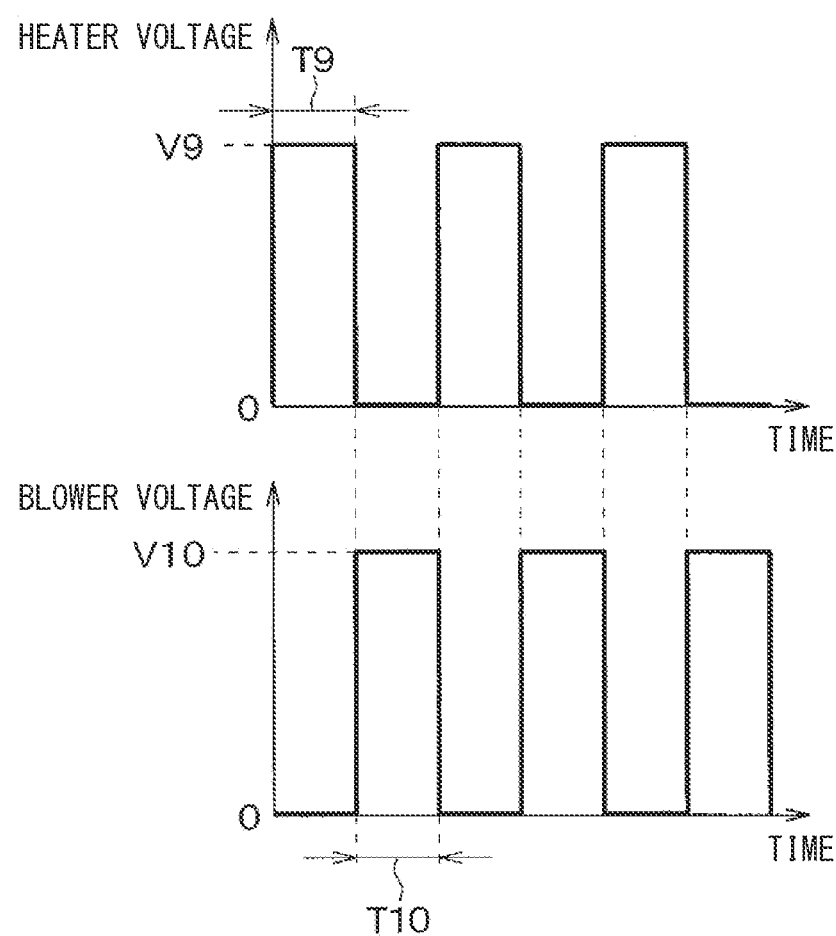
FIG. 8E is a time chart illustrating the operation contents of the seat heater and the blower when the fatigue level of the third embodiment is 5.

In the present embodiment, in the memory of the HCU 20, respective operation contents illustrated in FIGS. 8A, 8B, 8C, 8D, and 8E are stored in advance as the operation contents of a seat heater 12 and a blower 14 in accordance with an estimated fatigue level. FIG. 8A indicates the operation contents when the fatigue level is 1. FIG. 8B indicates the operation contents when the fatigue level is 2. FIG. 8C indicates the operation contents when the fatigue level is 3. FIG. 8D indicates the operation contents when the fatigue level is 4. FIG. 8E indicates the operation contents when the fatigue level is 5.

In the correlation among FIGS. 8A to 8E, the relationship among heater voltages, the relationship among blower voltages, the relationship among the operating times of the seat heater 12, and the operating times of the blower 14 are established as follows:

$$V1<V3<V5<V7<V9$$

$$V2<V4<V6<V8<V10$$

$$T1<T3<T5<T7<T9$$

$$T2<T4<T6<T8<T10$$

In the respective operation contents illustrated in FIGS. 8A to 8E, as the estimated fatigue level becomes higher, a heater voltage and the operating time of the seat heater 12 in the hot-stimulation supply state increase, and a blower voltage and the operating time of the blower 14 in the cold-stimulation supply state also increase. Thus, also in the present embodiment, the stimulation amounts of hot stimulation and cold stimulation received by a passenger increase as the fatigue level becomes higher, as described in the first and second embodiments.

Figure 9:
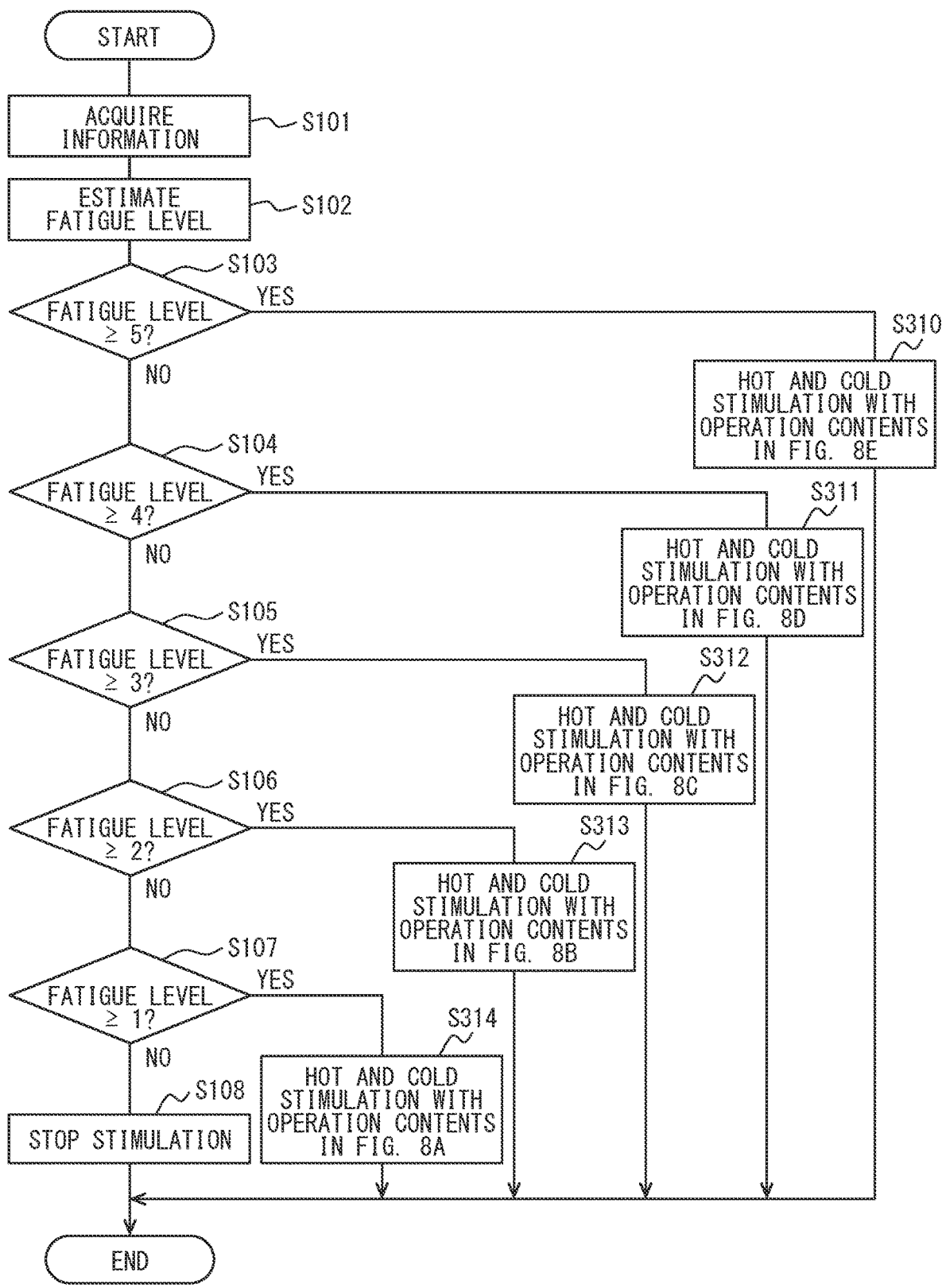
FIG. 9 is a flowchart illustrating the control processing of an HCU according to the third embodiment.

The HCU 20 performs control processing illustrated in FIG. 9. The control processing illustrated in FIG. 9 is different from the control processing illustrated in FIG. 5 in that steps S110, S111, S112, S113, and S114 are replaced with steps S310, S311, S312, S313, and S314, respectively. Steps S310, S311, S312, S313, and S314 correspond to a control unit that controls the operation of a stimulation supply unit so as to supply the hot stimulation and the cold stimulation alternately to the subject in accordance with the fatigue level estimated by an estimation unit.

When the fatigue level estimated in step S102 is 5, the HCU 20 in step S310 transmits, to a seat ECU 18, an operation instruction to perform the hot and cold stimulation according to the operation contents in FIG. 8E that correspond to the fatigue level of 5. The seat ECU 18 operates each of the seat heater 12 and the blower 14 according to the operation contents in FIG. 8E.

When the fatigue level estimated in step S102 is 4, the HCU 20 in step S311 transmits, to the seat ECU 18, an operation instruction to perform the hot and cold stimulation according to the operation contents in FIG. 8D that correspond to the fatigue level of 4. The seat ECU 18 operates each of the seat heater 12 and the blower 14 according to the operation contents in FIG. 8D.

When the fatigue level estimated in step S102 is 3, the HCU 20 in step S312 transmits, to the seat ECU 18, an operation instruction to perform the hot and cold stimulation according to the operation contents in FIG. 8C that correspond to the fatigue level of 5. The seat ECU 18 operates each of the seat heater 12 and the blower 14 according to the operation contents illustrated in FIG. 8C.

When the fatigue level estimated in step S102 is 2, the HCU 20 in step S313 transmits, to the seat ECU 18, an operation instruction to perform the hot and cold stimulation according to the operation contents in FIG. 8B that correspond to the fatigue level of 5. The seat ECU 18 operates each of the seat heater 12 and the blower 14 according to the operation contents illustrated in FIG. 8B.

When the fatigue level estimated in step S102 is 1, the HCU 20 in step S314 transmits, to the seat ECU 18, an operation instruction to perform the hot and cold stimulation according to the operation contents in FIG. 8A that correspond to the fatigue level of 5. The seat ECU 18 operates each of the seat heater 12 and the blower 14 according to the operation contents illustrated in FIG. 8A.

As described above, according to the heating and cooling stimulation device 10 of the present embodiment, the HCU 20 in steps S310 to S314 controls the operation of the seat heater 12 such that the intensity of the hot stimulation supplied by the seat heater 12 is increased and the operating time of the seat heater 12 during which the seat heater 12 supplies the hot stimulation is elongated as the estimated fatigue level becomes higher. The HCU 20 controls the operation of the blower 14 such that the intensity of the cold stimulation supplied by the blower 14 is increased and the operating time of the blower 14 during which the blower 14 supplies the cold stimulation is elongated as the estimated fatigue level becomes higher. In this way, the HCU 20 controls the operations of the seat heater 12 and the blower 14 such that the amount of the hot stimulation received by the passenger and the amount of the cold stimulation received by the passenger increase as the estimated fatigue level becomes higher. Thus, also in the present embodiment, the same effect as the first embodiment is obtained.

Fourth Embodiment

In the present embodiment, control processing performed by an HCU 20 is partially changed from that of the first embodiment. Other configurations of a heating and cooling stimulation device 10 are identical to those of the first embodiment. Different points from the first embodiment will be described below.

Figure 10A:
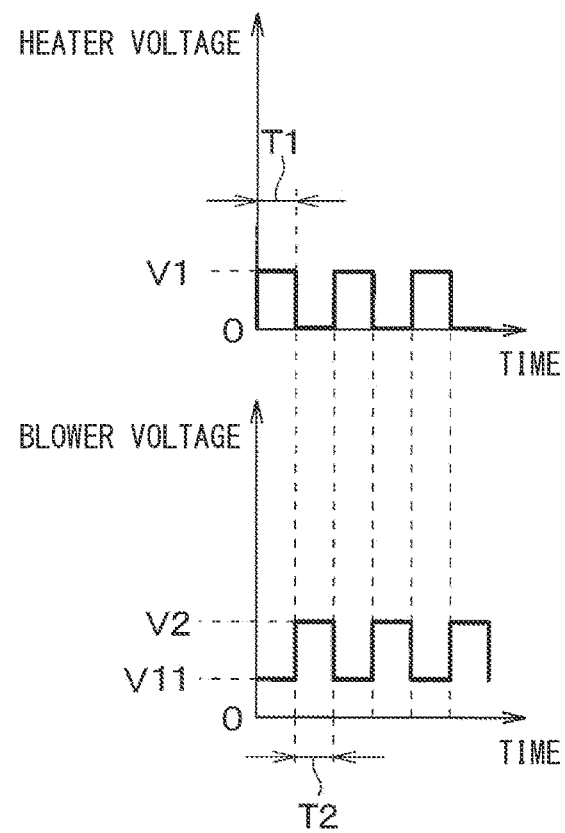
FIG. 10A is a time chart illustrating the operation contents of a seat heater and a blower when the fatigue level of a fourth embodiment is 1.
Figure 10B:
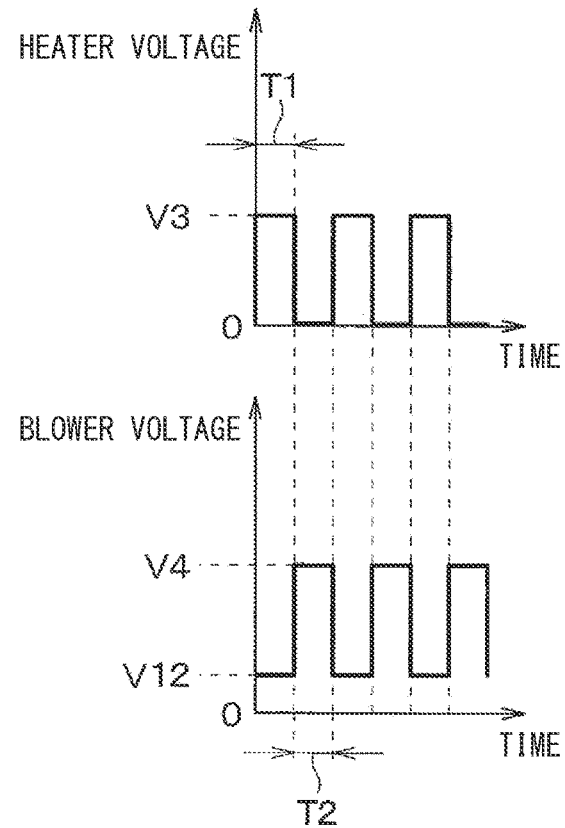
FIG. 10B is a time chart illustrating the operation contents of the seat heater and the blower when the fatigue level of the fourth embodiment is 2.
Figure 10C:
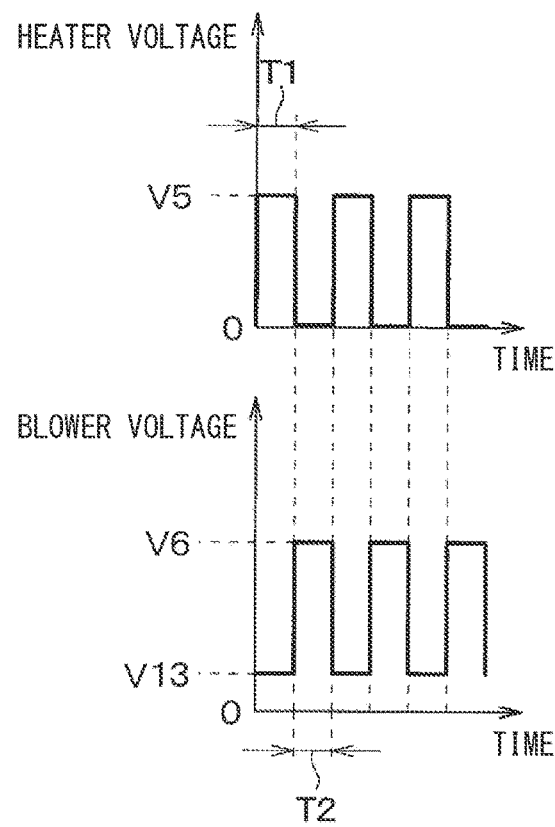
FIG. 10C is a time chart illustrating the operation contents of the seat heater and the blower when the fatigue level of the fourth embodiment is 3.
Figure 10D:
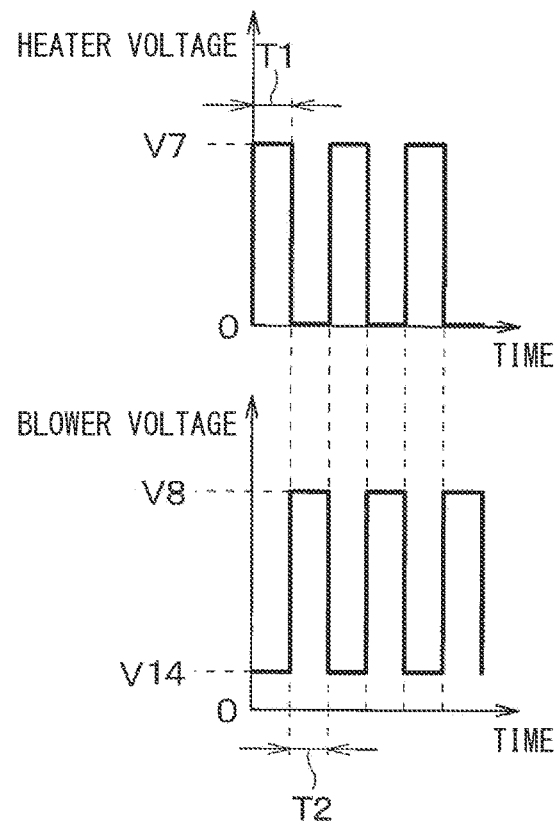
FIG. 10D is a time chart illustrating the operation contents of the seat heater and the blower when the fatigue level of the fourth embodiment is 4.
Figure 10E:
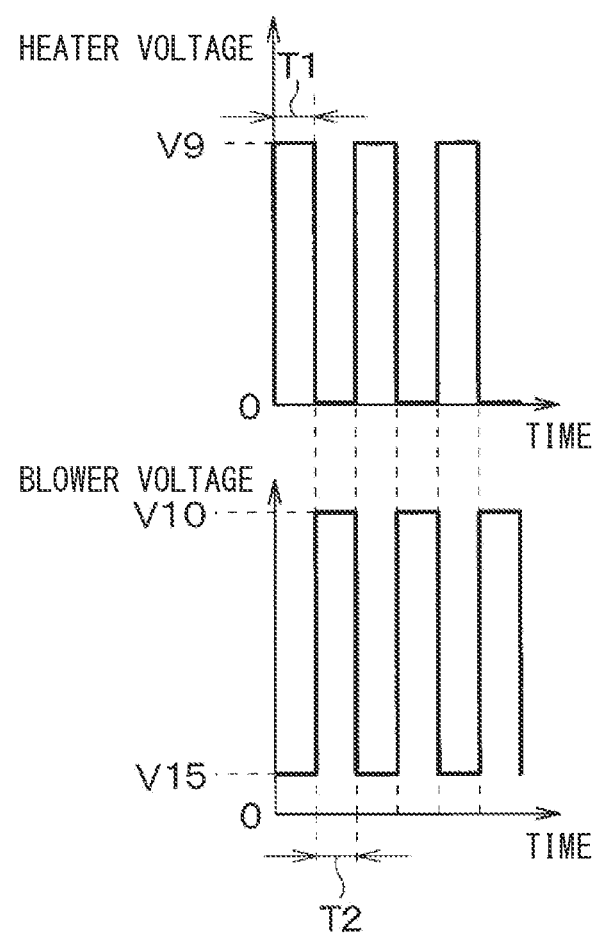
FIG. 10E is a time chart illustrating the operation contents of the seat heater and the blower when the fatigue level of the fourth embodiment is 5.

In the present embodiment, in the memory of the HCU 20, respective operation contents illustrated in FIGS. 10A, 10B, 10C, 10D, and 10E are stored in advance as the operation contents of each of a seat heater 12 and a blower 14 in accordance with an estimated fatigue level. FIG. 10A indicates the operation contents when the fatigue level is 1. FIG. 10B indicates the operation contents when the fatigue level is 2. FIG. 10C indicates the operation contents when the fatigue level is 3. FIG. 10D indicates the operation contents when the fatigue level is 4. FIG. 10E indicates the operation contents when the fatigue level is 5.

In the correlation among FIGS. 10A to 10E, the relationship among the magnitudes of V1, V3, V5, V7, and V9 is identical to that of the first embodiment. The relationship among the magnitudes of V2, V4, V6, V8, and V10 is identical to that of the first embodiment.

Figure 11:
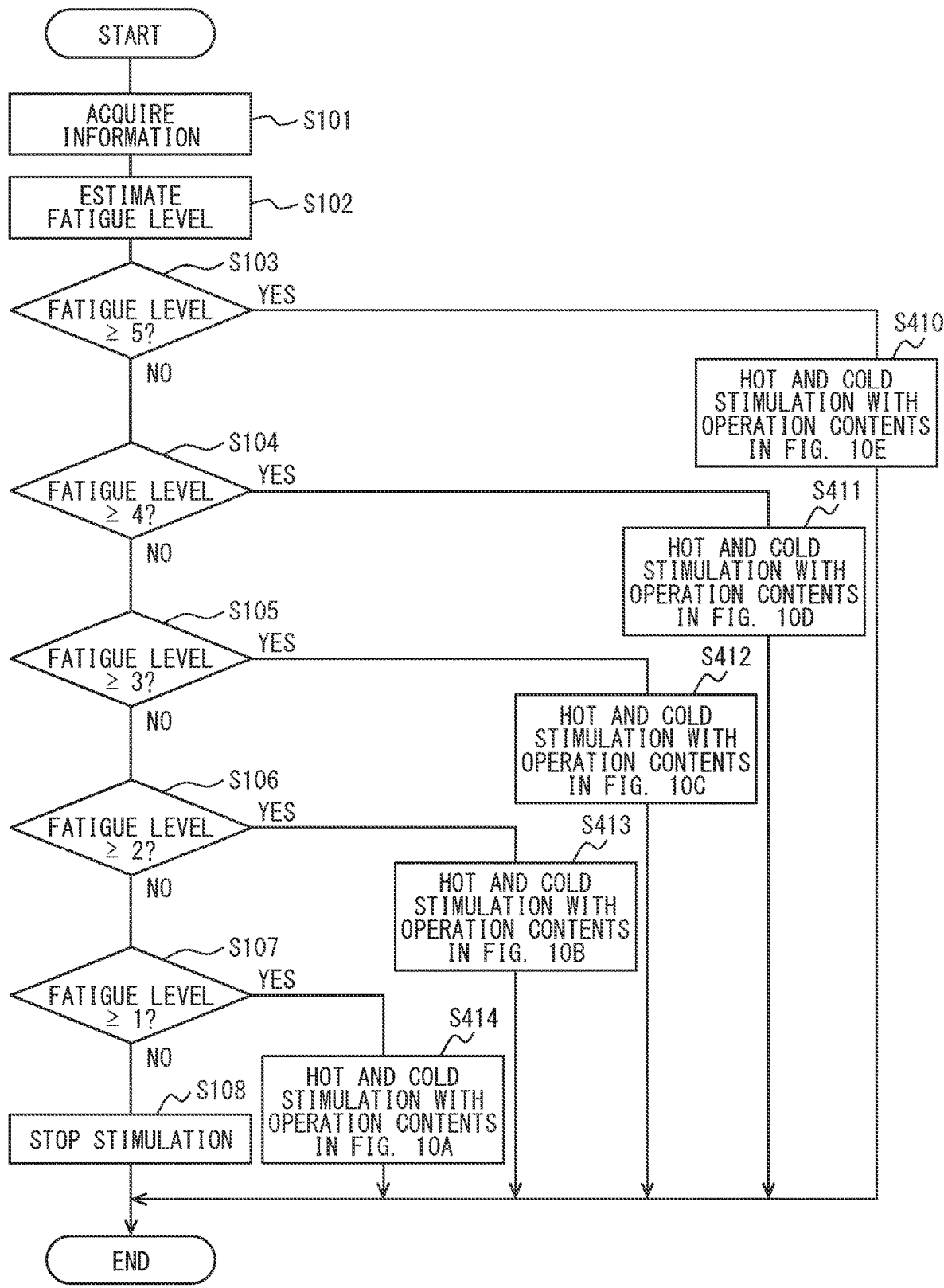
FIG. 11 is a flowchart illustrating the control processing of an HCU according to the fourth embodiment.

The HCU 20 performs control processing illustrated in FIG. 11. The control processing illustrated in FIG. 11 is different from the control processing illustrated in FIG. 5 in that steps S110, S111, S112, S113, and S114 are replaced with steps S410, S411, S412, S413, and S414, respectively. Steps S410, S411, S412, S413, and S414 correspond to a control unit that controls the operation of a stimulation supply unit so as to supply hot stimulation and cold stimulation alternately to a subject in accordance with a fatigue level estimated by an estimation unit.

In the first embodiment, in the hot-stimulation supply state where a heater voltage is "large" and a blower voltage is "small," the blower voltage is set at 0. In present embodiment, as illustrated in FIGS. 10A to 10E, blower voltages are V11, V12, V13, V14, and V15 in a hot-stimulation supply state. V11 to V15 are small values larger than 0 and enable the supply of hot stimulation to a passenger by an operation of the seat heater 12 even when the blower 14 is operated. V11 to V15 may be equal to one another or different from one another.

In this way, the blower 14 may be operated if the hot stimulation is supplied to the passenger when the seat heater 12 supplies the hot stimulation to the passenger. Also in the present embodiment, the same effect as the first embodiment is obtained.

Fifth Embodiment

In the present embodiment, control processing performed by an HCU 20 is partially changed from that of the first embodiment. Other configurations of a heating and cooling stimulation device 10 are identical to those of the first embodiment. Different points from the first embodiment will be described below.

Figure 12A:
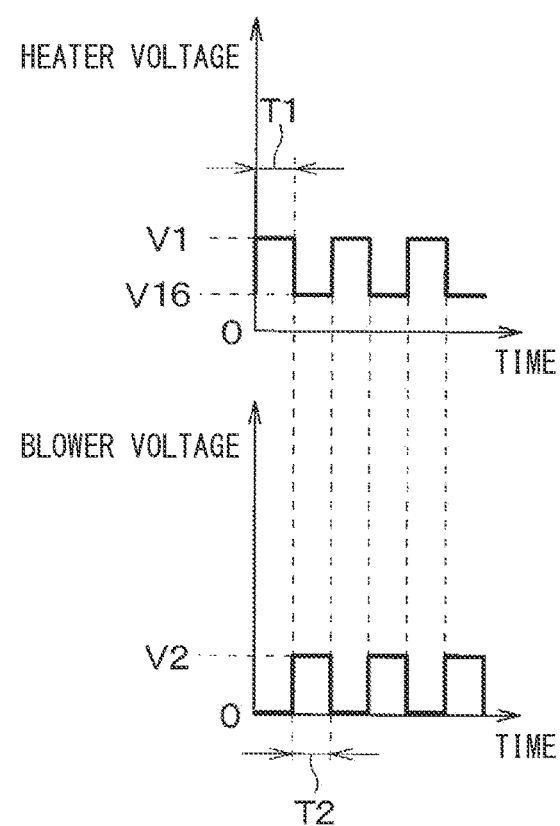
FIG. 12A is a time chart illustrating the operation contents of a seat heater and a blower when the fatigue level of a fifth embodiment is 1.
Figure 12B:
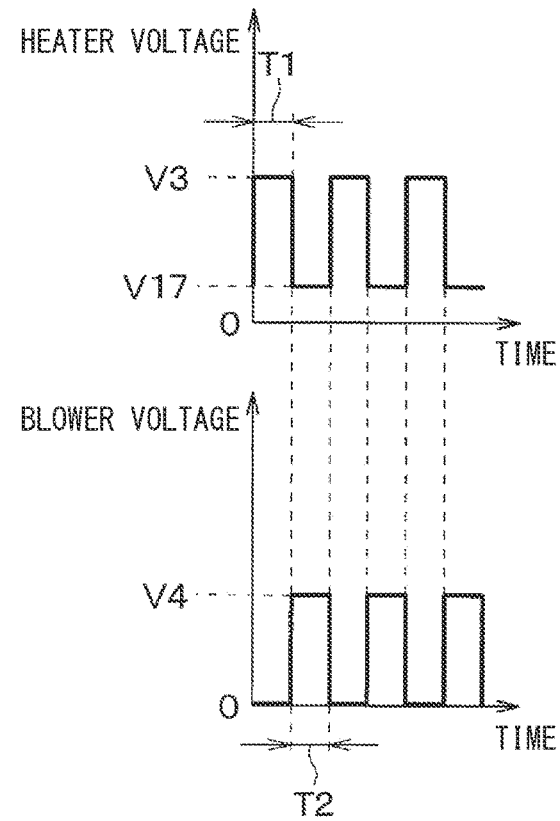
FIG. 12B is a time chart illustrating the operation contents of the seat heater and the blower when the fatigue level of the fifth embodiment is 2.
Figure 12C:
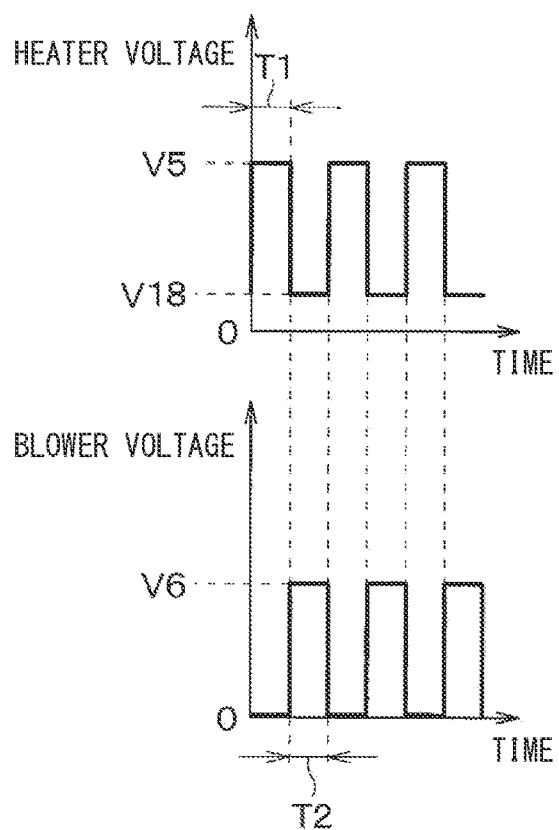
FIG. 12C is a time chart illustrating the operation contents of the seat heater and the blower when the fatigue level of the fifth embodiment is 3.
Figure 12D:
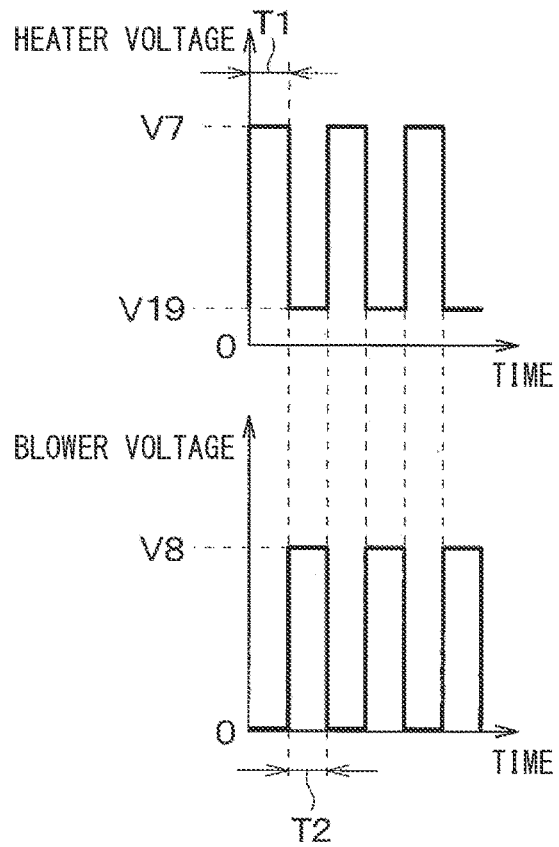
FIG. 12D is a time chart illustrating the operation contents of the seat heater and the blower when the fatigue level of the fifth embodiment is 4.

In the present embodiment, in the memory of the HCU 20, respective operation contents illustrated in FIGS. 12A, 12B, 12C, 12D, and 12E are stored in advance as the operation contents of each of a seat heater 12 and a blower 14 in accordance with an estimated fatigue level. FIG. 12A illustrates the operation contents when the fatigue level is 1. FIG. 12B illustrates the operation contents when the fatigue level is 2. FIG. 12C indicates the operation contents when the fatigue level is 3. FIG. 12D indicates the operation contents when the fatigue level is 4. FIG. 12E indicates the operation contents when the fatigue level is 5.

In the correlation among FIGS. 12A to 12E, the relationship among the magnitudes of V1, V3, V5, V7, and V9 is identical to that of the first embodiment. The relationship among the magnitudes of V2, V4, V6, V8, and V10 is identical to that of the first embodiment.

Figure 13:
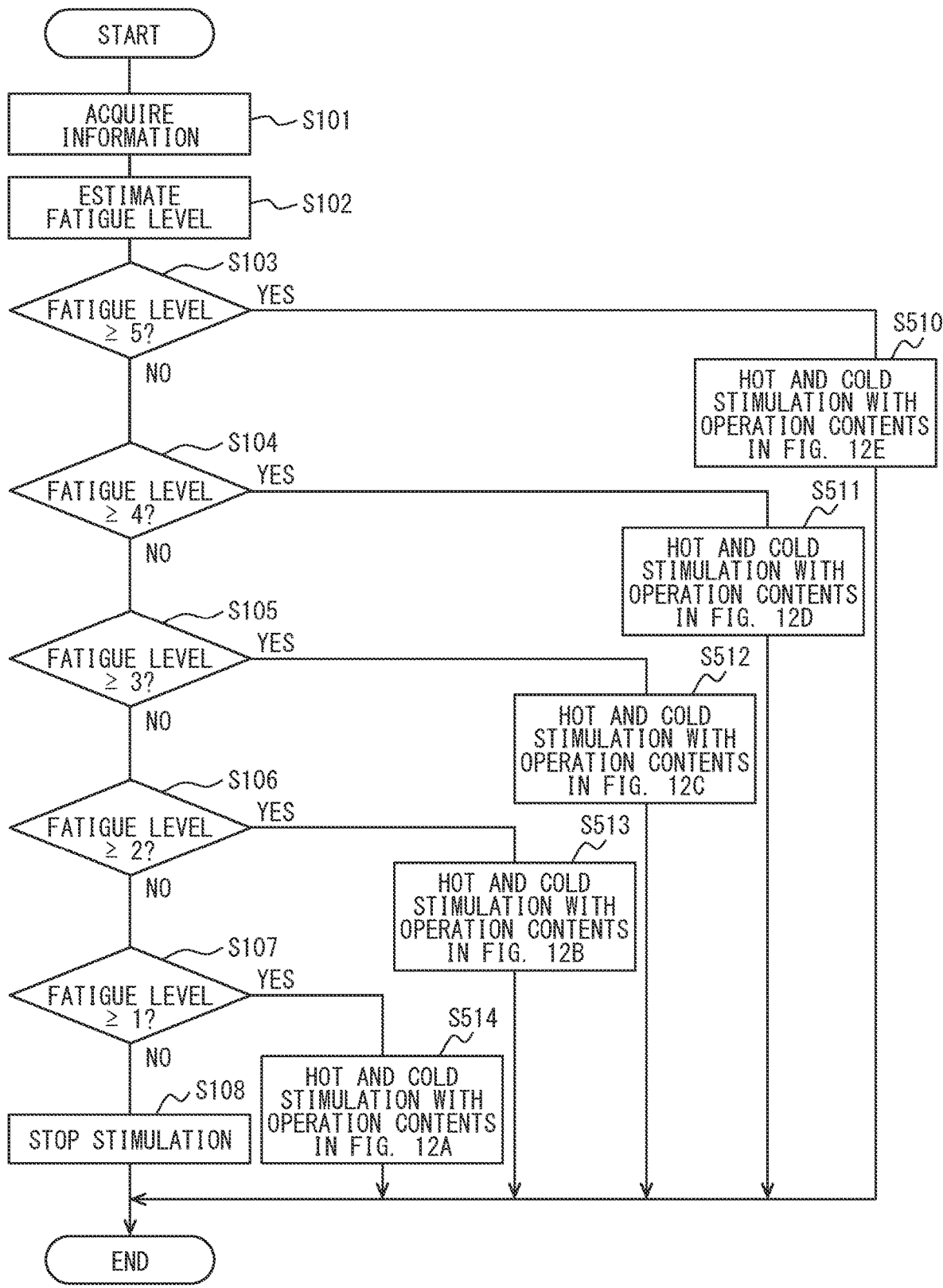
FIG. 13 is a flowchart illustrating the control processing of an HCU according to the fifth embodiment.

The HCU 20 performs control processing illustrated in FIG. 13. The control processing illustrated in FIG. 13 is different from the control processing illustrated in FIG. 5 in that steps S110, S111, S112, S113, and S114 are replaced with steps S510, S511, S512, S513, and S514, respectively. Steps S510, S511, S512, S513, and S514 correspond to a control unit that controls the operation of a stimulation supply unit so as to supply hot stimulation and cold stimulation alternately to a subject in accordance with a fatigue level estimated by an estimation unit.

In the first embodiment, in a cold-stimulation supply state where a heater voltage is "small" and a blower voltage is "large," the heater voltage is set at 0. In present embodiment, as illustrated in FIGS. 12A to 12E, heater voltages are V16, V17, V18, V19, and V20 in the cold-stimulation supply state. V16 to V20 are small values larger than 0 and enable the supply of the cold stimulation to a passenger by an operation of the blower 14 even when the seat heater 12 is operated.

In this way, the seat heater 12 may be operated if the hot stimulation is supplied to the passenger when the cold stimulation is supplied to the passenger by the operation of the blower 14. Also in the present embodiment, the same effect as the first embodiment can be obtained.

Sixth Embodiment

In the present embodiment, control processing performed by an HCU 20 is partially changed from that of the first embodiment. Other configurations of a heating and cooling stimulation device 10 are identical to those of the first embodiment.

In the first embodiment, operation contents illustrated in FIG. 4E are stored in the memory of the HCU 20 in advance as operation contents for a fatigue level of 5. When the fatigue level is 5, the HCU 20 in step S110 transmits the operation contents illustrated in FIG. 4E to the seat ECU 18. The seat ECU 18 operates each of the seat heater 12 and the blower 14 according to the operation contents illustrated in FIG. 4E.

Figure 14:
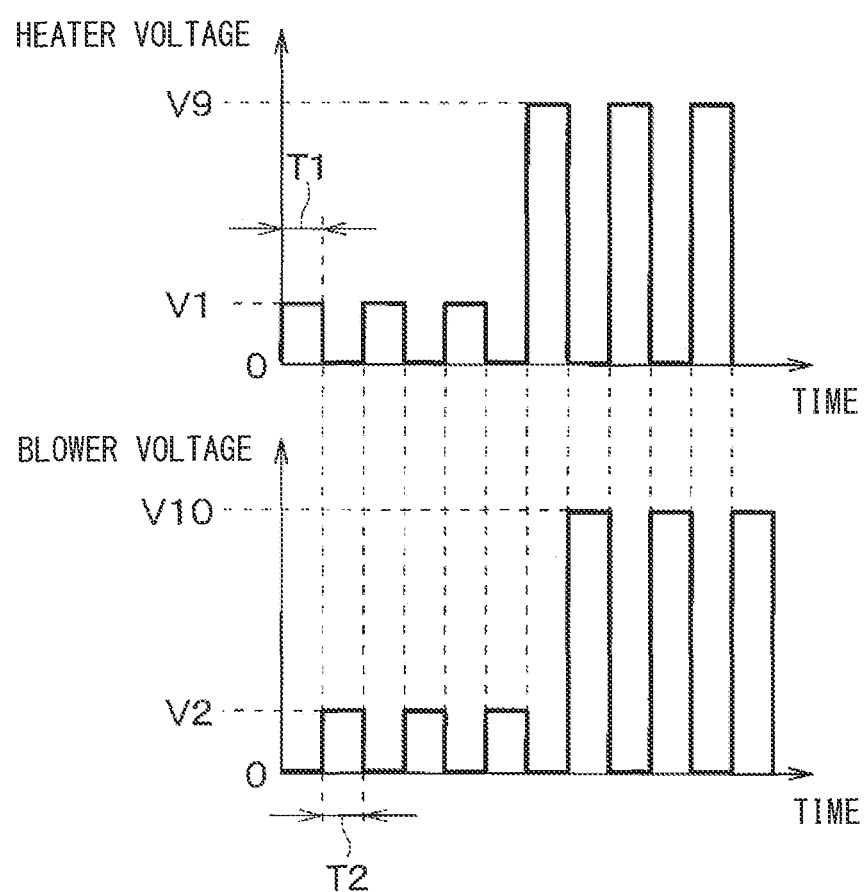
FIG. 14 is a time chart illustrating the operation contents of a seat heater and a blower when the fatigue level of a sixth embodiment is 5.

In contrast, in the present embodiment, operation contents illustrated in FIG. 14 are stored in the memory of the HCU 20 in advance as operation contents for a fatigue level of 5. When the fatigue level is 5, the HCU 20 transmits the operation contents illustrated in FIG. 14 to a seat ECU 18. The seat ECU 18 operates each of a seat heater 12 and a blower 14 according to the operation contents illustrated in FIG. 14.

The operation contents illustrated in FIG. 14 include a heater voltage of V1 in a hot-stimulation supply state and a blower voltage of V2 in a cold-stimulation supply state in an initial stage until after the lapse of a predetermined time immediately after the start of supply of hot and cold stimulation. V1 and V2 in FIG. 14 are equivalent to V1 and V2 in FIG. 4A. V1 and V2 in FIG. 14 may be other small voltages regardless of the fatigue level.

Thereafter, the heater voltage in the hot-stimulation supply state is set at V9, and the blower voltage in the cold-stimulation supply state is set at V10. V9 and V10 in FIG. 14 are equivalent to V9 and V10 in FIG. 4E. V9 and V10 in FIG. 14 are large voltages that are set according to the fatigue level.

In this way, in the present embodiment, the HCU 20 initially performs initial control when the fatigue level is high. In the initial control, the hot and cold stimulation is performed such that the intensity of the hot stimulation and the intensity of the cold stimulation are each set at predetermined low initial intensity regardless of the fatigue level. The HCU 20 then performs control for performing the hot and cold stimulation such that the intensity of the hot stimulation and the intensity of the cold stimulation are each set higher than the initial intensity that is preset according to the fatigue level.

Thus, even if the fatigue level is high, the hot stimulation with low intensity and the cold stimulation with low intensity are supplied alternately to a passenger in the initial stage. Thereafter, the hot stimulation with high intensity and the cold stimulation with high intensity in accordance to the fatigue level are supplied alternately to the passenger.

According to the present embodiment, after the initial stage, the hot stimulation and the cold stimulation are supplied to the passenger with high intensity in accordance with the fatigue level. Hence, the same effect as the first embodiment is obtained.

Furthermore, the present embodiment also obtains the following effects. Specifically, if the hot stimulation and cold stimulation are supplied with high intensity immediately after the start of the supply unlike in the present embodiment, a passenger may feel uncomfortable.

According to the present embodiment, in the initial stage, the hot stimulation and the cold stimulation are supplied with low intensity regardless of the fatigue level. Thus, the discomfort of the passenger can be suppressed.

In the present embodiment, the initial control is performed when the fatigue level is 5. However, the initial control may be performed when the fatigue level is not 5.

Other Embodiments (1) In the foregoing embodiments, the HCU 20 controls the respective operations of the seat heater 12 and the blower 14 such that the amount of hot stimulation and the amount of cold stimulation that are received by the passenger increase as the fatigue level estimated in step S102 becomes higher. However, the HCU 20 may control the respective operations of the seat heater 12 and the blower 14 such that only the amount of cold stimulation increases from among the amount of hot stimulation and the amount of cold stimulation. This control can also obtain the same effect as the first embodiment.

However, the respective operations of the seat heater 12 and the blower 14 are more preferably controlled so as to increase the amount of hot stimulation and the amount of cold stimulation. In this case, the amount of cold stimulation and the amount of hot stimulation that are received by the subject increase as the fatigue level becomes higher. Thus, as compared with the case in which only the amount of cold stimulation increases from among the amount of cold stimulation and the amount of hot stimulation, a difference between the amount of hot stimulation and the amount of cold stimulation is made larger, thereby enhancing the effect of improving a blood flow.

(2) In the foregoing embodiments, the HCU 20 transmits the operation contents to the seat ECU 18 in accordance with the estimated fatigue level. The seat ECU 18 operates each of the seat heater 12 and the blower 14 according to the transmitted operation contents. However, the HCU 20 may operate each of the seat heater 12 and the blower 14 according to the operation contents corresponding to the fatigue level. Specifically, the HCU 20 may directly control the respective operations of the seat heater 12 and the blower 14 so as to supply hot stimulation and cold stimulation alternately to the passenger in accordance with the estimated fatigue level.

(3) In the foregoing embodiments, the seat heater 12 and the blower 14 are provided in the backrest portion 103 of the seat 101. However, the seat heater 12 and the blower 14 may be provided in the seating portion 102 of the seat 101.

(4) In the foregoing embodiments, the seat heater 12 and the blower 14 are provided in the driver's seat 101. However, the seat heater 12 and the blower 14 may be provided in a seat other than the driver's seat.

(5) In the foregoing embodiments, the seat heater 12 and the blower 14 are used as stimulation supply units that supply hot stimulation and cold stimulation to the subject. However, other units may be used as stimulation supply units. For example, a unit that circulates a heating medium for providing heating or cooling for the subject may be used. Alternatively, a thermoelectric transducer or a heat exchanger for providing heating or cooling for the subject may be used. Moreover, a unit for blowing warm air to the subject may be used as a configuration for supplying hot stimulation in the stimulation supply unit. Furthermore, a unit for blowing cold air to the subject may be used as a configuration for supplying cold stimulation in the stimulation supply unit.

(6) In the foregoing embodiments, the stimulation supply unit is installed in the seat of the vehicle. However, the stimulation supply unit may be installed in the seat of a mobile unit other than a vehicle. Alternatively, the stimulation supply unit may be installed in a seat other than the seat of a mobile unit. Alternatively, the stimulation supply unit may be installed in a location other than a seat. The stimulation supply unit may be a compact and portable unit that is not installed in a specific location. Alternatively, the stimulation supply unit may be attached to the subject. For example, the stimulation supply unit may be attached to a shoulder, the waist, or an arm of the subject.

(7) In the foregoing embodiments, the HCU 20 acquires information inputted by a touch panel operation by the passenger, as information on the fatigue level in step S101 for the control processing of the HCU 20. In step S102, the HCU 20 estimates the fatigue level of the passenger based on the information acquired. However, the HCU 20 may estimate the fatigue level of the passenger based on other information on the fatigue level.

The other information includes information obtained by inputting voice from the passenger. For example, an agent asks the passenger about the fatigue level via external communications. The passenger answers the question by voice. At this point, the passenger's voice illustrating the fatigue level is inputted from a microphone. In this case, in S101, the HCU 20 acquires the voice. In step S102, the HCU 20 may analyze the voice and estimate the fatigue level.

Further, the other information includes a seating time that is an elapsed time from the start of seating by the passenger on the seat 101. As the seating time is elongated, the fatigue level becomes higher. Thus, the HCU 20 acquires the seating time by using a seating sensor or the like. The HCU 20 may estimate the fatigue level of the passenger based on the acquired seating time.

Furthermore, the other information includes biological information on the passenger. For example, the HCU 20 acquires the heart rate of the passenger, the heart rate being detected by a heart rate sensor. A predetermined relationship is established between the heart rate and the fatigue level. The HCU 20 may estimate the fatigue level based on the acquired heart rate of the passenger.

Moreover, the other information includes information on the behaviors of the vehicle during driving. If the fatigue level of the passenger becomes higher during the driving of the vehicle, lane changes or variations in distance between vehicles increase. Thus, the HCU 20 may acquire information on vehicle behaviors and estimate the fatigue level based on the acquired information on vehicle behaviors.

(8) The present disclosure is not limited to the foregoing embodiments. The present disclosure can be optionally changed and also includes various modifications or variations within the equivalent range. Moreover, the foregoing embodiments are not irrelevant to one another. The embodiments can be optionally combined except that the combination is apparently prohibited. In the foregoing embodiments, the elements constituting the embodiments are not always necessary unless otherwise specified as necessary elements or unless otherwise noted as theoretically necessary elements. In the foregoing embodiments, if numeric values such as the number, numeric values, amounts, and ranges of the constituent elements of the embodiments are referred to, the present disclosure is not limited to the specific numeric values unless otherwise specified as necessary numeric values or unless otherwise noted as theoretically necessary numeric values.

(9) The HCU 20 and the technique according to the present disclosure may be implemented by a dedicated purpose computer that is provided by including a processor programmed to perform one or more features incorporated by a computer program and memory. Alternatively, the HCU 20 and the technique according to the present disclosure may be implemented by a dedicated purpose computer that is provided by configuring a processor with at least one dedicated hardware logic circuit. Alternatively, the HCU 20 and the technique according to the present disclosure may be implemented by at least one dedicated purpose computer that includes a combination of the processor programmed to perform one or more features and the memory and the at least one dedicated hardware logic circuit. The computer program may be stored in a computer-readable non-transitory tangible recording medium as an instruction to be executed by a computer.

CONCLUSION

According to a first aspect described in some or all of the embodiments, a heating and cooling stimulation device includes: a stimulation supply unit that supplies hot stimulation and cold stimulation to a subject; an estimation unit that estimates the fatigue level of the subject; and a control unit that controls an operation of the stimulation supply unit so as to supply the hot stimulation and the cold stimulation alternately to the subject in accordance with the fatigue level estimated by the estimation unit. The control unit controls the operation of the stimulation supply unit such that an amount of the cold stimulation received by the subject increases as the fatigue level estimated by the estimation unit becomes higher.

According to a second aspect, the control unit controls the operation of the stimulation supply unit such that the amount of the cold stimulation received by the subject increases by increasing the intensity of the cold stimulation supplied by the stimulation supply unit as the fatigue level estimated by the estimation unit becomes higher. As a specific configuration of the first aspect, the second aspect can be used.

According to a third aspect, the control unit controls the operation of the stimulation supply unit such that the amount of the cold stimulation received by the subject increases by elongating the operating time of the stimulation supply unit during which the stimulation supply unit supplies the cold stimulation as the fatigue level estimated by the estimation unit becomes higher. As a specific configuration of the first aspect, the third aspect can be used.

According to a fourth aspect, the control unit controls the operation of the stimulation supply unit such that the amount of the hot stimulation received by the subject increases as the fatigue level estimated by the estimation unit becomes higher. With this configuration, the amount of cold stimulation and the amount of hot stimulation that are received by the subject increase as the fatigue level becomes higher. Thus, as compared with the case in which only the amount of cold stimulation increases from among the amount of cold stimulation and the amount of hot stimulation, a difference between the amount of hot stimulation and the amount of cold stimulation is made larger, thereby enhancing the effect of improving a blood flow.

According to a fifth aspect, the control unit controls the operation of the stimulation supply unit such that the amount of the hot stimulation received by the subject increases by increasing the intensity of the hot stimulation supplied by the stimulation supply unit as the fatigue level estimated by the estimation unit becomes higher. As a specific configuration of the fourth aspect, the fifth aspect can be used.

According to a sixth aspect, the control unit controls the operation of the stimulation supply unit such that the amount of the hot stimulation received by the subject increases by elongating the operating time of the stimulation supply unit during which the stimulation supply unit supplies the hot stimulation as the fatigue level estimated by the estimation unit becomes higher. As a specific configuration of the fourth aspect, the sixth aspect can be used.

What is claimed is:

1. A heating and cooling stimulation device, comprising:
a stimulation supply unit configured to supply hot stimulation and cold stimulation to a subject;
an estimation unit configured to estimate a fatigue level of the subject; and
a control unit configured to control an operation of the stimulation supply unit and to perform an alternate control in which the hot stimulation and the cold stimulation are alternately supplied in sequence to the subject, wherein
the control unit controls the operation of the stimulation supply unit, to increase an amount of the cold stimulation received by the subject in the alternate control as the fatigue level estimated by the estimation unit becomes higher.

2. The heating and cooling stimulation device according to claim 1, wherein the control unit controls the operation of the stimulation supply unit, to increase the amount of the cold stimulation received by the subject increases by increasing an intensity of the cold stimulation supplied by the stimulation supply unit as the fatigue level estimated by the estimation unit becomes higher.

3. The heating and cooling stimulation device according to claim 1, wherein the control unit controls the operation of the stimulation supply unit, to increase the amount of the cold stimulation received by the subject by elongating an operating time of the stimulation supply unit during which the stimulation supply unit supplies the cold stimulation, as the fatigue level estimated by the estimation unit becomes higher.

4. The heating and cooling stimulation device according to claim 1, wherein the control unit controls the operation of the stimulation supply unit, to increase an amount of the hot stimulation received by the subject as the fatigue level estimated by the estimation unit becomes higher.

5. The heating and cooling stimulation device according to claim 4, wherein the control unit controls the operation of the stimulation supply unit, to increase the amount of the hot stimulation received by the subject by increasing an intensity of the hot stimulation supplied from the stimulation supply unit, as the fatigue level estimated by the estimation unit becomes higher.

6. The heating and cooling stimulation device according to claim 4, wherein the control unit controls the operation of the stimulation supply unit, to increase the amount of the hot stimulation received by the subject by elongating an operating time of the stimulation supply unit during which the stimulation supply unit supplies the hot stimulation, as the fatigue level estimated by the estimation unit becomes higher.

7. A heating and cooling stimulation device, comprising:
a stimulation supply unit configured to supply hot stimulation and cold stimulation to a subject; and
a controller configured to estimate a fatigue level of the subject, and configured to control an operation of the stimulation supply unit and to perform an alternate control in which the hot stimulation and the cold stimulation are alternately supplied in sequence to the subject, wherein
the controller increases an amount of the cold stimulation supplied from the stimulation supply unit to the subject in the alternate control as the estimated fatigue level becomes higher, and decreases the amount of the cold stimulation supplied from the stimulation supply unit to the subject in the alternate control as the estimated fatigue level becomes lower.

8. The heating and cooling stimulation device according to claim 7, wherein the controller increases the amounts of the cold stimulation and the hot stimulation supplied from the stimulation supply unit to the subject as the estimated fatigue level becomes higher, and decreases the amounts of the cold stimulation and the hot stimulation supplied from the stimulation supply unit to the subject as the estimated fatigue level becomes lower.

9. The heating and cooling stimulation device according to claim 7, wherein the stimulation supply unit includes a heater configured to supply the hot stimulation, and a blower configured to supply the cold stimulation.

10. The heating and cooling stimulation device according to claim 9, wherein the heater and the blower are both provided only in a backrest portion of a seat.

11. The heating and cooling stimulation device according to claim 7, wherein
the controller increases a difference of the amount of the cold stimulation and an amount of the hot stimulation received by the subject in the alternate control, by increasing the amount of the cold stimulation received by the subject in the alternate control, as the estimated fatigue level becomes higher.

12. The heating and cooling stimulation device according to claim 1, wherein
the control unit is configured to increase a difference of the amount of the cold stimulation and an amount of the hot stimulation received by the subject in the alternate control, by increasing the amount of the cold stimulation received by the subject in the alternate control, as the fatigue level estimated by the estimation unit becomes higher.

13. The heating and cooling stimulation device according to claim 1, wherein the stimulation supply unit includes a heater configured to supply the hot stimulation and a blower configured to supply the cold stimulation.

14. The heating and cooling stimulation device according to claim 13, wherein the heater and the blower are both provided only in a backrest portion of a seat.

* * * * *